(12) United States Patent
Chandelier et al.

(10) Patent No.: US 9,717,414 B2
(45) Date of Patent: Aug. 1, 2017

(54) METHOD AND APPARATUS FOR ISOLATING A POTENTIAL ANOMALY IN IMAGING DATA AND ITS APPLICATION TO MEDICAL IMAGERY

(75) Inventors: Florent André Robert Chandelier, Granby (CA); Thomas Bernard Pascal Vincent, Brossard (CA)

(73) Assignee: DOG MICROSYSTEMS INC., Granby, Quebec (CA)

( * ) Notice: Subject to any disclaimer, the term of this patent is extended or adjusted under 35 U.S.C. 154(b) by 0 days.

(21) Appl. No.: 14/001,628

(22) PCT Filed: Feb. 24, 2012

(86) PCT No.: PCT/CA2012/000172
§ 371 (c)(1),
(2), (4) Date: Sep. 18, 2013

(87) PCT Pub. No.: WO2012/113069
PCT Pub. Date: Aug. 30, 2012

(65) Prior Publication Data
US 2014/0010430 A1 Jan. 9, 2014

Related U.S. Application Data

(60) Provisional application No. 61/446,342, filed on Feb. 24, 2011.

(51) Int. Cl.
*A61B 5/00* (2006.01)
*G06T 7/00* (2017.01)
(Continued)

(52) U.S. Cl.
CPC .......... *A61B 5/0033* (2013.01); *A61B 6/5217* (2013.01); *G06T 7/0012* (2013.01);
(Continued)

(58) Field of Classification Search
None
See application file for complete search history.

(56) References Cited

U.S. PATENT DOCUMENTS 6,331,116 B1 * 12/2001 Kaufman ............... G06K 9/209
345/418
6,549,646 B1 4/2003 Yeh
(Continued)

FOREIGN PATENT DOCUMENTS

| WO | WO 98/37517 | 8/1998 |
|---|---|---|
| WO | WO/2011/063493 | 6/2011 |
| WO | WO/2011/063495 | 6/2011 |

OTHER PUBLICATIONS

Gokturk et al., "A Statistical 3D Pattern Processing Method for Computer-Aided Detection of Polyps in CT Colonography," IEEE Transactions on Medical Imaging, vol. 20, No. 12, Dec. 2001.
(Continued)

*Primary Examiner* — Tsung-Yin Tsai
(74) *Attorney, Agent, or Firm* — Pearl Cohen Zedek Latzer Baratz LLP

(57) ABSTRACT

A method for isolating a potential anomaly in imaging data comprising: providing a set of at least one given anomaly property representative of a given anomaly; providing a anomaly property identifier for identifying each of the at least one given anomaly property; in the imaging data, isolating a first zone having a first property and a group of at least one other zone, each of the at least one other zone having a corresponding property different than the first property; in the imaging data, and resulting from the isolation of a first zone and a group of at least one other zone, providing a transition zone selected from a group consisting of: a closed zone separating the first zone and the group of at least one other zone; and a closed zone extending in one of the first zone and the group of at least one other zone;
(Continued)

applying the anomaly property identifier for identifying each of the at least one given anomaly property on at least the transition zone for providing a computed indication for a selected zone, the selected zone being at least the transition zone; determining if the computed indication for the selected zone is concording with each of the at least one given anomaly property; and if the computed indication for the selected zone is concording, assigning an indication of potential anomaly candidate zone to the selected zone to thereby isolate the potential anomaly.

18 Claims, 19 Drawing Sheets

(51) Int. Cl.
 *A61B 6/00* (2006.01)
 *A61B 8/08* (2006.01)
(52) U.S. Cl.
 CPC .............. *A61B 6/463* (2013.01); *A61B 8/5223* (2013.01); *G06T 2207/10081* (2013.01); *G06T 2207/30032* (2013.01); *G06T 2207/30096* (2013.01); *G06T 2207/30101* (2013.01)

(56) References Cited

U.S. PATENT DOCUMENTS

| | | | |
|---|---|---|---|
| 7,113,617 B2 | 9/2006 | Kimmel | |
| 7,236,620 B1* | 6/2007 | Gurcan | G06K 9/46 378/4 |
| 7,346,209 B2 | 3/2008 | Beaulieu | |
| 7,369,638 B2 | 5/2008 | Kiraly | |
| 7,440,601 B1 | 10/2008 | Summers | |
| 7,447,342 B2* | 11/2008 | Cathier | G06T 7/0012 378/21 |
| 8,724,894 B1* | 5/2014 | Jensen | G06T 11/001 358/529 |
| 2004/0064029 A1 | 4/2004 | Summers | |
| 2004/0223633 A1* | 11/2004 | Krishnan | G06F 19/321 382/128 |
| 2005/0107691 A1* | 5/2005 | Zalis | G06T 5/50 600/425 |
| 2009/0016583 A1 | 1/2009 | Lakare | |
| 2010/0021026 A1* | 1/2010 | Collins | G06K 9/00 382/128 |
| 2010/0183210 A1* | 7/2010 | Van Uitert | G06K 9/46 382/131 |

OTHER PUBLICATIONS

G. Kindlmann et al., "Semi-Automatic Generation of Transfer Functions for Direct Volume Rendering," IEEE Symposium on Volume Visualization, 1998.
J. Näppi et al., "Fully Automated Three-Dimensional Detection of Polyps in Fecal-Tagging CT Colonography," Acad.Radiol., 14(3), pp. 287-300, Mar. 2007.
J.A. Sethian, "Evolution, Implementation, and Application of level set and fast marching methods for advancing front," Journal of Computational Physics, vol. 169, pp. 503-555, 2001 (Dept. of Mathematics, University of California, Feb. 20, 2000).
P.I. Corke et al., "Fast Image Segmentation," Dept. of Computer & Information Science, School of Engineering and Applied Science, University of Pennsylvania, Philadelphia, Jul. 1989.
J.K. Udupa et al., "Fuzzy Connectedness and Image Segmentation," Proceedings of the IEEE, vol. 91, No. 10, pp. 1649-1669, Oct. 2003.
E. Davies, "Machine Vision: Theory, Algorithms and Practicalities," Academic Press, Sep. 1990, Chap. 6.
R. Kimmel et al., "Sub-pixel Distance Maps and Weighted Distance Transforms," Journal of Mathematical Imaging and Vision, 1994.
Gibson, Sarah F.F., "Using Distance Maps for Accurate Surface Representation in Sampled Volumes," Mitsubishi Electric Research Laboratory, IEEE, Dec. 1999.
International Search Report for International Application No. PCT/CA2012/000172 mailed May 1, 2012.
Barnes, Eric, "Virtual colonoscopy CAD finds most cancers," AuntMinnie.com, Apr. 3, 2009.

* cited by examiner

METHOD AND APPARATUS FOR ISOLATING A POTENTIAL ANOMALY IN IMAGING DATA AND ITS APPLICATION TO MEDICAL IMAGERY

CROSS-REFERENCE TO RELATED APPLICATIONS

This application is a National Phase Application of PCT International Application No. PCT/CA2012/000172, International Filing Date Feb. 24, 2012, which claims priority of US Provisional Patent Application No. 61/446,342, entitled "Method and apparatus for isolating a potential anomaly in imaging data and its application to medical imagery", that was filed Feb. 24, 2011, the entire content of which is incorporated by reference.

FIELD OF THE INVENTION

This invention relates to data processing. More precisely, the invention pertains to a method and a system for image processing, in particular to computer-aided detection and diagnosis (CADe and CADx respectively) of medical datasets, more specifically for the detection of anomalies in hollow organs such as, but not restricted to, colorectal lesions or abdominal aortic aneurysms.

BACKGROUND

In medicine, CAD systems are meant to ultimately output potential anomalies within medical images. Prior art methods and systems have typically gathered 2D and 3D approaches with a preferred and most successful process being a coarse to fine approach, detecting multiple "coarse" initial patches further refined by a classifier that only the "best" candidates may survive.

A first method for polyp identification in the colon is disclosed in International PCT application No. WO 98/37517 entitled "Automatic analysis in virtual endoscopy". The proposed methods and systems require the segmentation of an organ of interest, typically a colon. Upon successful segmentation, a mesh, i.e. a set of isosurfaces oriented from normals, is used to interactively visualize the colon, in addition to support a "shape characteristics analysis" comprising the step of determining a convexity value for each population representing an amount and direction of curvature.

Such method and the equivalent subsequent ones that were proposed, such as the one disclosed in U.S. Pat. No. 7,369,638, base their strategy on the identification of characteristic shapes of polyps when compared to the smooth appearance of the colonic mucosa for example. Thus, an accurate representation of the organ based on a segmentation process is required in order to accurately identify shapes of interest. The skilled addressee will appreciate that lesions of random shapes may not be detected. For the case of CT colonography, also called virtual colonoscopy, the skilled addressee will appreciate that most prior art methods are meant to identify polypoid anomalies (of spherical shapes), not cancers neither masses (of random shapes with potentially no spherical protuberance).

However, and as mentioned in U.S. Pat. No. 7,236,620 (hereinafter '620) entitled "Computer-aided detection methods in volumetric imagery", detectors based on curvature calculation use derivative processes which are susceptible to produce spurious outputs due to noise in the input imagery. Such limitation also affect every equivalent method involving gradient and iso-surfaces considering that the zero value iso-surface of the distance map yields the object surface and the derivative of the distance map yields the surface normal, i.e. a mesh, as mentioned in 1998, Using distance maps for accurate surface representation in sampled volumes, Gibson Sarah F. F., Mitsubishi Electric Research Laboratory, IEEE. The skilled addressee will appreciate that any such distance map requires object segmentation, as stated in U.S. Pat. No. 7,113,617 entitled "Method of computing sub-pixel Euclidean distance maps". As mentioned, a method of generating a distance map includes the step of identifying a boundary curve of a source image. The skilled addressee will appreciate that, for the case of CAD methods in CT Colonography for example, prior art segmentation and distance map determinations rely on the accurate identification of the inner wall of the colonic mucosa on which surface normals are determined (such as mesh, gradient).

To overcome the above-mentioned limitations of "derivative processes", '620 patent discloses a method based on simple spherical summations. The method requires a binary image, i.e. segmented, to be input, from which a shape is defined based on the ratio of segmented elements falling within the ratio of two spherical summation processes, involving one 2D image at a time but overlooking a 3D region. Such methodology does reduce the amount of processing time required and is less susceptible to noise, but is still really dependent on the image segmentation processing. As such, it only decreases the processing time and complexity required, but does not improve the detection output as it shifts the difficulty toward the segmentation stage.

Concurrently, Gokturk introduced a three-dimensional pattern recognition method to detect shapes in medical images at the Biomedical computation Stanford 2000 symposium proceedings entitled "recognizing polyps from 3D CT colon data" where a random slicing through a candidate volume is used in order to extract shape features from 2D slices, the latter being input in a support vector machine (SVM) classifier further in charge to identify polyp candidates. This was further detailed in "A statistical 3D pattern processing method for computer-aided detection of polyps in CT colonography, Gokturk and al., IEEE transaction on medical imaging, vol. 20(12) December 2001" and led to U.S. Pat. No. 7,346,209. These developments lead to an approach similar to that of '620 patent involving the use of 2D gradient summations in order to reduce noise artifacts, expecting that summation and smoothing operations would help enhance the difference between homogeneous and inhomogeneous structures, where local image gradient at pixels other than edges would be more significant than it would be for homogeneous structures. As such, a limitation arises in the definition of the edges, which is the necessity to have an accurate segmentation process of the structure of interest. Additionally, Gokturk methods were more about constructing shape signatures to be further input in classifiers than polyp detection in itself.

Following both preceding concepts and combining them, Cathier disclosed a method and system for using cutting planes for colon polyp detection in U.S. Pat. No. 7,447,342 (hereinafter '342). The method and system disclosed involve the reslicing of volumes throughout a dataset in order to detect small and round shaped traces on any of these planes. However, and as the previous techniques discussed herein, this method requires that the image be preprocessed to distinguish the colon from other structures in the image with high accuracy necessary to successful polyp detection. Furthermore, the skilled addressee will appreciate that such technique is meant to be used for polypoid shape recognition but does not address the needs of cancers and masses detection (featuring random shapes).

To overcome the limitation of '342 method with respect to its sensitivity to a binarization threshold, US Patent Application published under No. 2009/0016583 discloses the use of a Divergence Gradient Field Response (DGFR). As mentioned, such method allows for the detection of circles directly in the gradient domain, instead of edges or magnitude of the gradient as in the case of the '342 patent. However, two intrinsic limitations are expressed in such methodology. First, a Divergence Gradient Field Response identifies circles of given sizes and, as the size of the polyp to be found is not a-priori known, one needs to compute DGFR for a multitude of sub-volumes (sub-sampled volumes) covering the complete range of polyps sizes. Thus, a choice such as at which point to stop sub-sampling has to be made, thereby limiting the size of the smallest and largest polyp to be found. This is an issue of template matching techniques well known to the skilled addressee. The second limitation is that DGFR detects circles, although polyps might depict shapes more complex than simple circles. Unfortunately, this technique does not address the needs of cancers and masses detection (i.e. random shapes).

Furthermore, in addition to an always existing segmentation limitation, it may be observed that these methodologies have two distinct steps: candidate detection and false-positive reduction, whether through density analysis or shape analysis for example. As well, the above mentioned methods are meant to detect circular/ellipsoidal shapes to further detect polyps. It is to be understood that looking for a sphere in a digital dataset will be equivalent to either detect round shapes or detect local/global curvatures. There is thus a lack of methods suitable to detect lesions of various sizes and shapes, as expressed by Dr C. Robinson at 2009 European Congress of Radiology (ECR) in Vienna: "CAD algorithms were developed to detect polyps in the context of screening", which study was meant to investigate the performance of a commercial CADe device based on "reader adjustable sphericity-settings" for cancer candidates generation. The author said that "The CAD algorithm was applied to each dataset at four sphericity settings (0, 50, 75, 100). Seventy-five was the default manufacturer's setting, 100 (highest sphericity) detected a more curvy shape, and a single observer characterized all of the CAD marks". Respectively at sphericity settings of 0; 50; 75 and 100, the results in terms of "Sensitivity; False-Positive rate" were {90.2%; 65}, {88.6%; 57}, {87.1%; 45} and {74.2%; 24}. Such a high false-positive rate demonstrates the inability of such morphology-based algorithm to accurately identify cancers and other lesions of varying shapes, considering high sensitivity may only be achieved if anything else (not of clinical interest) is picked. This is well expressed by Dr. C. Robinson: "The detection of cancer increases with decreasing sphericity, at the expense of decreasing specificity."

Finally, amongst other limitations is the fact that some methods involve simple threshold to distinguish the colon from other structure to differentiate the lumen from tissues. Although there is no such "simple threshold" method, a clear limitation of such methods would be the inability to handle CT colonography datasets resulting from reduced preparation with fluid/stool tagging where more than "simply separating air/tissue" is required. Indeed, and considering such reduced preparation, the skilled addressee will understand that tagged-residual might represent small/round characteristics similar to polyps.

It would therefore be desirable to provide an improved method and apparatus that will overcome at least one of the above-identified drawbacks.

BRIEF SUMMARY

It is therefore an object of the present invention to provide a method and a system for isolating potential anomalies and use thereof for hollow organs in medical datasets.

It is another object of the present invention to provide such method and system for assisting automated detection of anomalies without prior accurate organ segmentation and without prior morphological knowledge of the anomalies.

According to one embodiment, there is provided a method for isolating a potential anomaly in imaging data, the method comprising providing a set of at least one given anomaly property representative of a given anomaly; providing an anomaly property identifier for identifying each of the at least one given anomaly property; in the imaging data, isolating a first zone having a first property and a group of at least one other zone, each of the at least one other zone having a corresponding property different than the first property; providing a transition zone resulting from the isolation of a first zone and a group of at least one other zone, the transition zone being selected from a group consisting of: a closed zone separating the first zone and the group of at least one other zone; and a closed zone extending in one of the first zone and the group of at least one other zone; applying the anomaly property identifier for identifying each of the at least one given anomaly property on at least the transition zone for providing a computed indication for a selected zone, the selected zone being at least the transition zone; determining if the computed indication for the selected zone is concording with each of the at least one given anomaly property and if the computed indication for the selected zone is concording, assigning an indication of potential anomaly candidate zone to the selected zone to thereby isolate said potential anomaly.

In accordance with one embodiment, the imaging data comprise a n-dimensional dataset originating from an imaging system, wherein n is greater or equal than two.

In accordance with another embodiment, the n-dimensional dataset is one of a 2-dimensional volumetric array of elements and a 3-dimensional volumetric array of elements.

In accordance with another embodiment, the n-dimensional dataset originates from a device selected from a group consisting of a magnetic resonance imaging (MRI) device, a positron emission tomography (PET) device, an X-Rays device, an ultrasound device and any combination thereof.

In accordance with another embodiment, the set of at least one given anomaly property comprises at least one of composition related information, shape related information, spatial localization in the imaging data, and a combination thereof over time.

In accordance with another embodiment, the anomaly property identifier comprises at least one of tissue density determination, homogeneity of tissue gradient determination, determination of absence or presence of tissue properties, determination of water content/distribution, determination of presence and determination of a distribution of contrast agent at a given moment or over time.

In accordance with an embodiment, the first property of the first zone comprises certain air region, the corresponding property of each of the at least one other zone comprises certain tissue region.

In accordance with another embodiment, the first property of the first zone comprises certain tagged region; the corresponding property of each of the at least one other zone comprises certain tissue region.

In accordance with another embodiment, the method further comprises applying the anomaly property identifier to the selected zone.

In accordance with another embodiment, the method further comprises providing an indication of a potential anomaly.

In accordance with another embodiment, the providing of an indication of a potential anomaly comprises at least one of storing the indication of a potential anomaly and displaying the indication of a potential anomaly on a user interface.

In accordance with another embodiment, the method further comprises transmitting the indication of a potential anomaly to a remote location.

In yet another embodiment, the image data comprises a plurality of unitary image elements selected from the group consisting of pixels and voxels.

In accordance with another embodiment, there is provided a machine readable medium having instructions recorded thereon for performing the method for isolating a potential anomaly in imaging data.

In accordance with another embodiment, there is provided a method for isolating a potential anomaly in imaging data, the method comprising receiving imaging data; isolating in the imaging data a first zone having a first property and a group of at least one other zone, each of the at least one other zone having a corresponding property different than the first property; providing a transition zone resulting from the isolation of a first zone and a group of at least one other zone, the transition zone being selected from a group consisting of a closed zone separating the first zone and the group of at least one other zone; and a closed zone extending in one of the first zone and the group of at least one other zone; applying an homogeneity of tissue gradient identifier on at least the transition zone for providing a computed indication for a selected zone, the selected zone being at least the transition zone; determining if the computed indication is concording for the selected zone; and if the computed indication for the selected zone is concording, assigning an indication of potential anomaly candidate zone to the selected zone to thereby isolate said potential anomaly.

In accordance with another embodiment, there is provided a system for isolating a potential anomaly in imaging data, the system comprising a data bus; a central processing unit operatively connected to the data bus; an I/O device operatively connected to the data bus; a network interface circuit operatively connected to the data bus; and a memory operatively connected to the data bus, the memory comprising at least one program for isolating a potential anomaly in imaging data wherein the at least one program is configured to be executed by the central processing unit, the at least one program for isolating a potential anomaly in imaging data comprising: instructions for providing an anomaly property identifier for identifying each of the at least one given anomaly property; instructions for isolating, in the imaging data, a first zone having a first property and a group of at least one other zone, each of the at least one other zone having a corresponding property different than the first property; instructions for providing a transition zone resulting from the isolation of a first zone and a group of at least one other zone, the transition zone being selected from a group consisting of a closed zone separating the first zone and the group of at least one other zone and a closed zone extending in one of the first zone and the group of at least one other zone; instructions for applying the anomaly property identifier for identifying each of the at least one given anomaly property on at least the transition zone for providing a computed indication for a selected zone, the selected zone being at least the transition zone; instructions for determining if the computed indication for the selected zone is concording with each of the at least one given anomaly property and if the computed indication for the selected zone is concording, for assigning an indication of potential anomaly candidate zone to the selected zone to thereby isolate said potential anomaly.

In accordance with another embodiment, there is provided a system for isolating a potential anomaly in imaging data, wherein the memory further comprises the imaging data.

In accordance with another embodiment, there is provided a system for isolating a potential anomaly, wherein the imaging data is received from the network interface circuit.

The method may be used for providing initial candidates or a complete detection scheme with efficient computational complexity and without requiring the organ of interest to be accurately segmented. This is of great advantage since the method may enhance detection of obstructive anomalies in hollow organs as well as other lesions in tortuous regions where an accurate segmentation required by prior art CAD methods may be difficult to achieve.

Moreover, the method is not dependent on restrictive shape analysis, nor is it dependent on a strict morphological feature analysis, such as curvature. This is of great advantage over the current state-of-the-art methods as lesions may depict variable shape and size. Although not depending on shape or morphological analysis features, the method may be combined with any of them as a subsequent classification process.

In one embodiment, the method may involve the use of uncertain regions, i.e. regions whose type is not known, also called transition regions, depicting partial volume artifact for example, by trying to extract some coherent information out-of it. This is of great advantage compared to prior art methods that aim at reducing, limiting or preventing any information from uncertain regions considering they carry predominantly presumably faulty signals.

BRIEF DESCRIPTION OF THE DRAWINGS

In order that the invention may be readily understood, embodiments of the invention are illustrated by way of examples in the accompanying drawings.

FIGS. 7A to 7D show images representative of a portion of a colon, according to one embodiment.

FIG. 18a & FIG. 18b) would discard false-positives due to air bubbles closed to the surface, potentially resulting from air in remnant stools for example.

FIG. 19 comprises a first image showing two regions under investigations, wherein one depicts a local maximum. FIG. 19 comprises an enlarged image in which coarse pixels of an original image can be seen.

Further details of the invention and its advantages will be apparent from the detailed description included below.

DETAILED DESCRIPTION

In the following description of the embodiments, references to the accompanying drawings are by way of illustration of examples by which the invention may be practiced. It will be understood that other embodiments may be made without departing from the scope of the invention disclosed.

As previously mentioned, CAD systems may be used in medicine for detecting potential anomalies on a given medical dataset. The present invention provides a method and an apparatus for isolating a potential anomaly in imaging data that may be particularly useful for detecting anomalies in hollow organs such as colorectal lesions or abdominal aortic aneurysms for non-limitative examples.

Although embodiments of the method will be described in a medical imagery application, the skilled addressee will nevertheless appreciate that various other applications may be envisaged, as it will become apparent upon reading of the present description.

Figure 1:
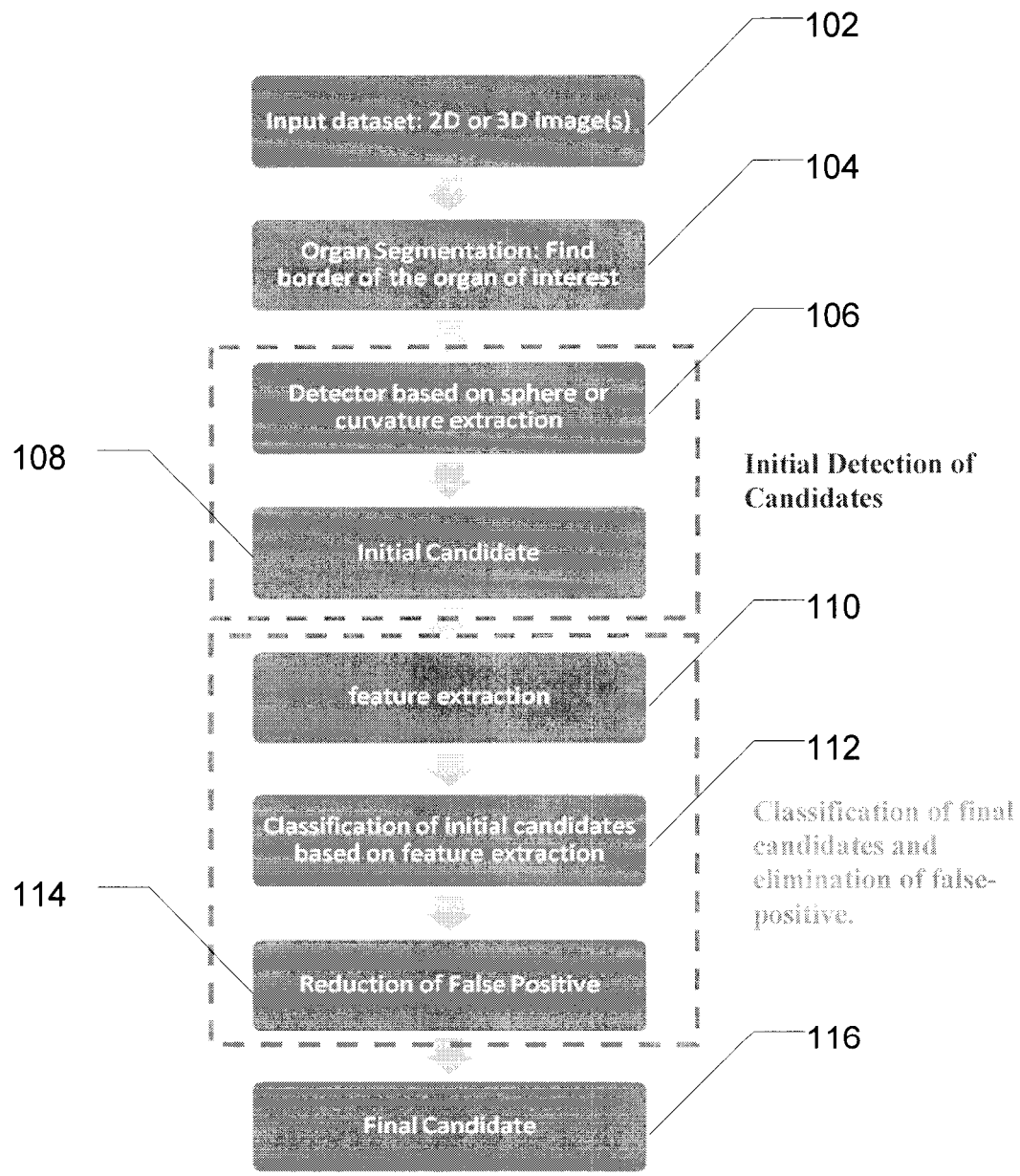
FIG. 1 (PRIOR ART) is a flow chart which shows a prior art method for providing final candidates in an anomalies detection scheme.

FIG. 1 shows a prior art method used for providing final candidates in an anomalies detection scheme. The method comprises an initial process for detecting the initial candidates, followed by a second process for providing the final candidates. As described below, the second process enables to classify the final candidates while trying to eliminate the false-positive candidates.

In the illustrated prior art method and according to processing step 102, an input dataset is provided. It will be appreciated that the input dataset may comprise 2D as well as 3D images, as known by the skilled addressee.

According to processing step 104, an organ segmentation is performed. The purpose of the organ segmentation is to suitably locate the border of the organ of interest.

According to processing step 106, a detection based on sphere or curvature extraction is performed.

According to processing step 108, initial candidates are provided. The initial candidates are provided following the detection.

According to processing step 110, a feature extraction is performed on the set of initial candidates.

According to processing step 112, a classification of initial candidates based on feature extraction is performed.

According to processing step 114, a reduction of false-positives is performed.

According to processing step 116, the final candidates are provided.

As previously mentioned and as it will become apparent below, contrary to the known prior art methods, the method of the present invention does not rely on an accurate segmentation of the organ of interest. The method may be used for providing either initial candidates or for providing a complete detection scheme with efficient computational complexity, as detailed thereinafter.

Indeed, in one embodiment, the described method does not depend on a restrictive shape analysis or a strict morphological feature analysis, both arising from the need of an accurate object segmentation for its potential detection, which is of great advantage since lesions to be found generally depict variable shape and size. The skilled addressee will nevertheless appreciate that the present method may be combined with any shape analysis or morphological feature analysis as a subsequent classification process, as it will become apparent below.

Now referring to FIG. 2, an embodiment of the method for isolating a potential anomaly in imaging data will now be described.

It will be appreciated that in one embodiment, the imaging data comprise a n-dimensional dataset (wherein n≥2) originating from an imaging system and provided to a processing system.

It will be appreciated by the skilled addressee that without restricting the dimension of such datasets, medical datasets are usually 2-dimensional or 3-dimensional volumetric array of elements, denoted as pixels and voxels respectively. Assuming an orthonormal coordinate system, a pixel element is represented along the axes (i,j) (respectively (i,j,k) for voxels) at the location (x,y) (respectively (x,y,z) for voxels). Consequently, a "slice" of a dataset may be selected by specifying a "z" location along the "k" axis of a 3-dimensional datasets.

Still in the embodiment of a medical imaging application, the datasets may be acquired from a device selected from a group consisting of a magnetic resonance imaging (MRI) device, a positron emission tomography (PET) device, an X-Rays device, an ultrasound device and any combination thereof. The acquired dataset comprises at least one portion of the organ of interest, for which each element can be related to a specific property of the human body. For example, a medical dataset acquired by a X-Ray CT scanner, comprising at least a portion of the colon, will depict elements with density values expressed in Hounsfield units and displayed in grayscaled colors, and where elements rendered in black will typically represent air-element of Hounsfield values below −400 Hu, thus allowing the visualization of hollow organs, such as the colon.

In one embodiment, as it will become apparent below, the method may involve the use of certain regions in the imaging data, i.e. regions which have been confidently detected as being of a particular known type such as bones, soft tissues, air regions and tagged regions, and the use of uncertain regions, i.e. regions depicting partial volume artifact for example. In this embodiment, the method uses at least the uncertain regions, also called transition zones, originating from the identification of the adjacent certain regions neighboring the uncertain regions in order to extract some coherent information. This is unlike other methods that aim at reducing, limiting or preventing any information from "uncertain" regions considering they carry predominantly presumably faulty signals.

For example and as it will be more detailed thereinafter, in one embodiment, the coherent information may be related to a property of a suspicious region to depict a concentric certain tissue type region surrounded by a certain air type region. Another exemplary property of a lesion is that it shows a homogeneous and concentric-denser tissue distribution.

The skilled addressee will appreciate that various other coherent information related to the properties of a potential lesion may be considered. For example, in the case the potential lesion depicts a coherent air density, coherent information showing the presence of air bubbles may be used to discard the potential lesion and identify it as a false positive, as better illustrated thereinafter. According to another typical characteristic of lesions, they may depict denser tissue in their center than in their surrounding. Lesions may also depict continuous properties such as denser and denser tissues without any other tissue types shock. Conversely, inhomogeneous remnant colonic fluids or fecal matter depict highly inhomogeneous tissue characteristics and the presence of trapped air bubbles. Nonetheless, typical lesions may also, in some cases, feature a surrounding high density tissue if coated within a tagging agent, such as Barium or Iodine for example. Finally, when considering intravenous acquisitions, lesions may depict tissue shocks due to higher centric densities considering lesions may be highly vascularized.

The skilled addressee will appreciate that various physiological properties or other types of property of colonic lesions may be of interest for implementing the method described therein in the given application of colorectal screening. The skilled addressee will also appreciate that other typical properties of a potential given anomaly may be derived from the clinical knowledge thereof, according to a given application field and to a given type of potential anomaly.

Figure 2:
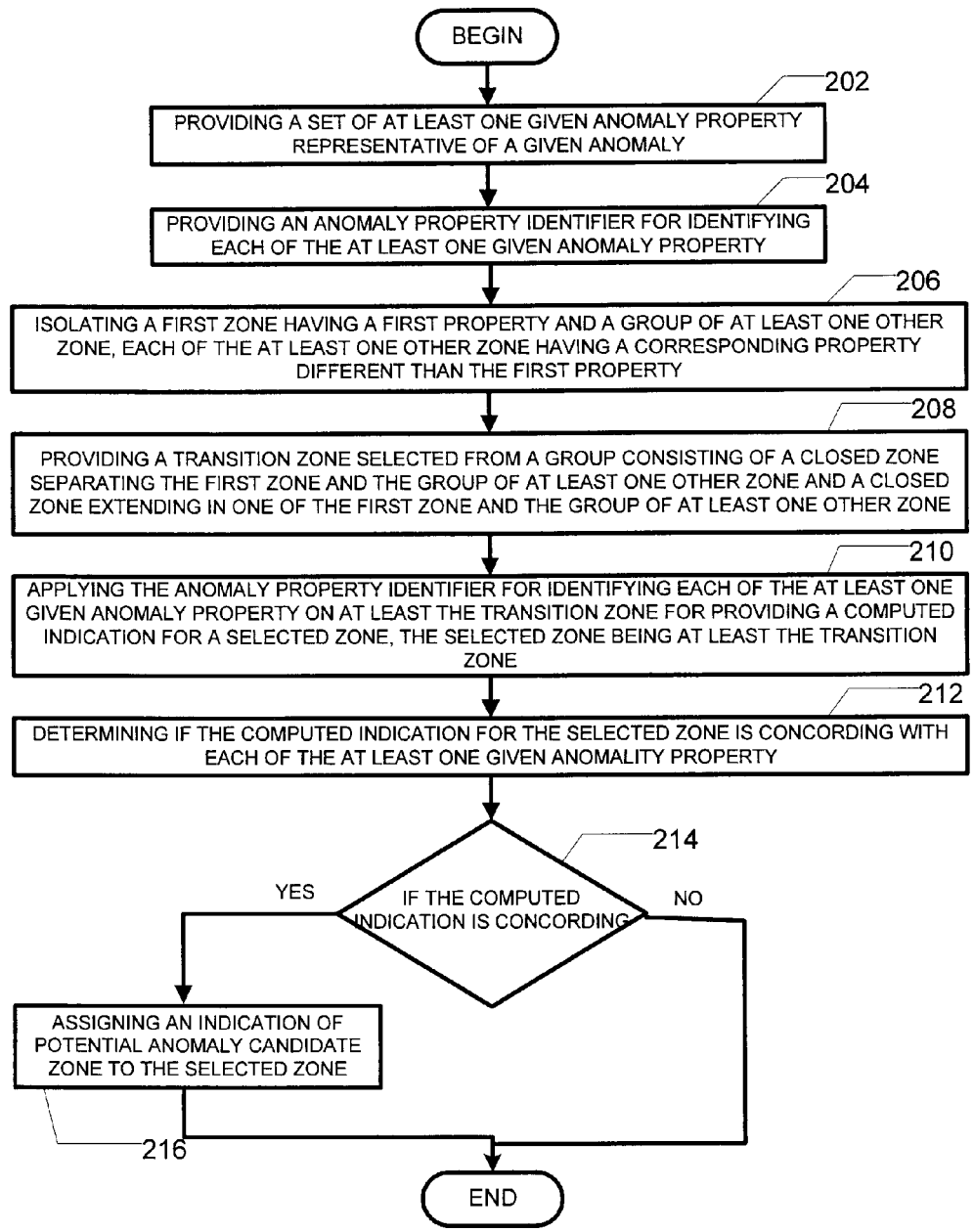
FIG. 2 is a flow chart which shows an embodiment of a method for isolating a potential anomaly in imaging data.

Still referring to FIG. 2 and according to processing step 202, a set of at least one given anomaly property representative of an anomaly is provided. In the example discussed above, the set of at least one given anomaly property may comprise one given anomaly property that is representative of a lesion, for example the given anomaly property may describe a concentric certain tissue type region whose density increases inwardly, surrounded by a certain air type region.

The skilled addressee will appreciate upon reading of the description that various other anomaly properties representative of a given lesion may be considered.

The skilled addressee will also appreciate that a given anomaly may be represented with a single one property as well as with a plurality of properties. For example, the set of at least one given anomaly property may comprise at least one of composition related information, shape related information, spatial localization in the imaging data and a combination thereof over time.

According to processing step 204, an anomaly property identifier for identifying each of the at least one given anomaly property is provided. In the embodiment described above, the anomaly property identifier may comprise the determination of a gradient, as it will become apparent below.

The skilled addressee will appreciate that various anomaly property identifier may be considered for the purpose of identifying a corresponding one anomaly property. It will also be appreciated that a combination of a plurality of anomaly property identifiers may be used according to a given application, as it will become apparent below. For example, in one embodiment, a first anomaly property identifier may be provided for identifying a first given anomaly property while a second anomaly property identifier may be provided for identifying a second given anomaly property.

As it will become apparent to the skilled addressee, the anomaly property identifier may comprise at least one of tissue density determination, homogeneity of tissue gradient determination, tissue distribution for a given region, determination of absence or presence of certain tissue properties, determination of water content/distribution for the case of MRI images, presence and distribution of contrast agent at a given moment or over time of acquisitions featuring intra-venous contrast agent.

In a further embodiment, intensity profile analysis comprising any derivative processes such as Gradient and Divergence analysis [Semi-Automatic Generation of Transfer Functions for Direct Volume Rendering, G. Kindlmann & J. W. Durkin, IEEE Symposium on Volume Visualization, 1998] and [Fully atutomated three-dimensional detection of polyps in fecal-tagging CT Colonography, J. Nappi, H. Yoshida, Acad. Radiol., 14(3)-287-300, March 2007], surface and volume distribution analysis comprising, but not limited to, distance transforms, intensity distributions, Euler front evolution [Evolution, Implementation, and Application of level set and fast marching methods for advancing front, J. A. Journal of computational Physics, 169:503-555, 2001] and Dynamic Front evolution theories such as advancing pareto fronts may be used.

The skilled addressee will appreciate that the anomaly property identifier may be derived from the image acquisition physics, the given anomaly physiology or a combination thereof, as it will become apparent upon reading of the present description. It will be appreciated that in one embodiment the anomaly property identifier is applied over a region preventing further dependence from segmentation processes.

It will be appreciated that tissue composition properties originate from the clinical understanding of any anomaly and the physics of image acquisitions, being density in Hounsfield values for CT scanners based on X-rays and water content in Magnetic Resonance Imaging as non limiting examples.

Still referring to FIG. 2 and according to processing step 206, a first zone and a group of at least one other zone are isolated in the imaging data.

It will be appreciated that the first zone has a first property. Moreover, it will also be appreciated that each zone of the group of at least one other zone has a corresponding property different than the first property, as detailed below.

For example and in one embodiment, the first zone may comprise a certain air region while the other zones of the group may comprise a certain tissue region.

In another embodiment, the first zone may comprise a certain tagged region, as it will be detailed thereinafter. It will be appreciated that certainty depends on the unambiguity of the information describing a given physical object (thus based on the physics of acquisition and understanding of the clinical aspects related such object). By means of non-exhaustive example, regions of Hounsfield vales below −500 most probably depict air regions.

According to processing step 208, and resulting from the isolation of a first zone and a group of at least one other zone, a transition zone is provided in the imaging data. The transition zone is selected from a group consisting of a closed zone separating the first zone and the group of at least one other zone and a closed zone extending in one of the first zone and the group of at least one other zone, as it will become apparent below.

In one embodiment and as mentioned above, the transition zone may be an uncertain region whose type is not known.

As it will become apparent below and in one embodiment, the transition zone is a closed zone in a 2D slice of imaging data. In the case where no closed zone may be provided in the slice of imaging data under analysis, the process of isolating a potential anomaly may be stopped without further processing and without isolating any potential anomaly, as better detailed thereinafter.

Figure 3:
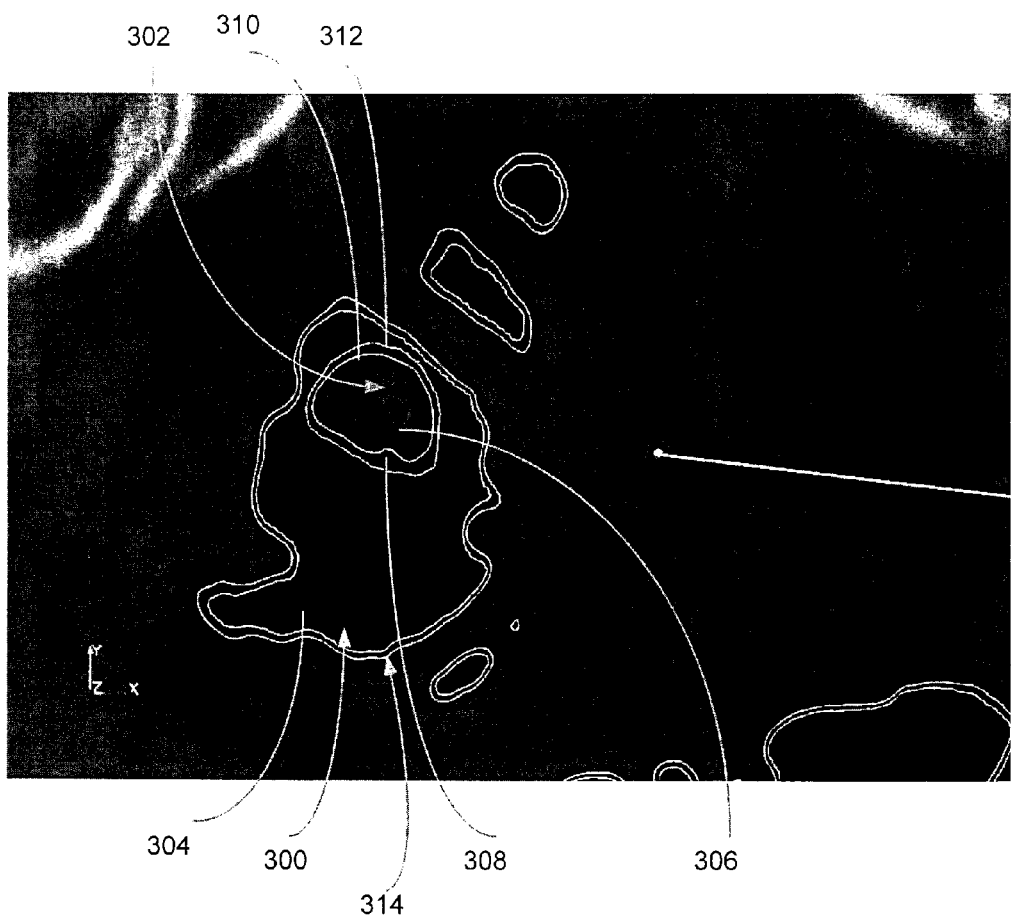
FIG. 3 is a CT scanned image showing a portion of a colon, according to one embodiment.

FIG. 3 shows an example of imaging data comprising a portion of a colon 300. The image data comprises a CT scanner Rx image which depicts a lesion 302. In this image, voxel elements which are darker depict air, voxel elements of grey intensity depict soft tissues and whitish elements depict bones or tagged tissues. As shown, the imaging data comprise a first zone 304 having a first property, at least one other zone 306 having a corresponding property different than the first property and a transition zone 308. In the illustrated embodiment, the first zone 304 is a certain air region totally surrounded by an adjacent closed transition zone 314. The other zone 306 is a certain tissue region entirely surrounded by the transition zone 308 which is a closed zone. The transition zones 308 and 314 comprise elements which have not been classified as belonging with certainty to a particular known type of elements.

Still referring to FIG. 2 and according to processing step 210, once the corresponding regions have been provided, the anomaly property identifier used for identifying each of the at least one given anomaly property is applied on at least the transition zone for providing a computed indication for a selected zone, the selected zone being at least the transition zone. As it will become apparent below to the skilled addressee, in one embodiment, the anomaly property identifier may also be applied on at least one of the certain zones in addition to the transition zone.

According to processing step 212, a determination is made as to whether the computed indication for the selected zone is concording with each of the at least one given anomaly property, as described below.

According to processing steps 214 and 216, if the computed indication for the selected zone is concording, an indication of potential anomaly candidate zone is assigned to the selected zone to thereby isolate the potential anomaly.

It will be appreciated that the indication of a potential anomaly may be provided according to various embodiments.

In particular the providing of the indication of a potential anomaly may comprise at least one of storing the indication of a potential anomaly and displaying the indication of a potential anomaly on a user interface.

It will be appreciated that the indication of a potential anomaly may be further transmitted to a remote location.

In one embodiment, the object of interest, i.e. the hollow organ, is defined and identified in the imaging data prior to isolating a potential anomaly. Prior art methods and systems mostly refer to such identification as a segmentation process, with purpose to isolate an organ and define with most accuracy its border (contour) such as the colonic mucosa. Such segmentation typically provides an object mask that may be binary with elements foreground representing the object and background representing a non-object zone [Fast image segmentation, P. I. Corke & H. I. Anderson, Dpt of computer and information science—school of engineering and applied science—university of Pennsylvania, Philadelphia, July 1989], even though this binary mask may arise from previous segmentation processes involving non-binary masks [Fuzzy connectedness and image segmentation, J. K. Udupa & P. K. Saha, IEEE, 91(10):1649-1669, October 2003].

As disclosed in co-pending PCT application by the same applicant No. PCT/CA2009/001749, entitled "Method for determining an estimation of a topological support of a tubular structure and use thereof in virtual endoscopy", and in PCT application No. PCT/CA2009/001743, entitled "Method and system for filtering image data and use thereof in virtual endoscopy", which are both incorporated herein by reference in their entireties, an appropriate support may be provided without using a segmentation process for identifying the object of interest. The described methods involve the definition of certainties masks that may encompass thick regions around the organ border. The skilled addressee will appreciate that in such embodiment different masks representing different regions with different certainties in terms of their belonging to the object of interest, supported by topological and connectivity considerations, are provided. The skilled addressee will appreciate that such embodiments may enable the providing of a complete CT Colonography system that does not introduce a segmentation process of the colon, but provide every information needed for the end-user to perform a colorectal cancer review on patient datasets, featuring state-of-the-art tools such as electronic colon cleansing.

In order to perform the detection of potential anomalies, as previously mentioned, various zones have to be provided. In one embodiment, different masks using different Window/Levels may be used on the imaging data for isolating a first zone and a group of at least one other zone and providing at least one transition zone. In a further embodiment, four masks may be used, respectively a colon mask, a bone mask, a lung mask and an abdominal mask. The anomaly property identifiers used for identifying each of the at least one given anomaly property may be applied at each Window/Levels.

Indeed, as it should be apparent to the skilled addressee, by applying the masks according to one of the corresponding methods known in the art to which the invention pertains, it is possible to roughly identify and label the different "connected-components" in each 2D slices of a relevant medical dataset [E. Davies *Machine Vision: Theory, Algorithms and Practicalities*, Academic Press, 1990, Chap. 6.]

The medical images may then be individually processed in order to identify disconnected non-air regions within air-regions, i.e. floating surfaces or unconnected regions. Potential anomaly detection may be performed as previously described for each such non-air region.

In another embodiment, the masks used for identifying the zones of interest may be obtained from certainty masks as provided in "Method for determining an estimation of a topological support or a tubular structure and use thereof in virtual endoscopy" and "Method and system for filtering image data and use thereof in virtual endoscopy" mentioned above.

For example, in one embodiment, the following masks are provided: high certainty air mask, high certainty Tag/Bone mask, uncertain mask for interfaces air/soft tissue, uncertain mask for interfaces tag/bone—soft tissue, uncertain mask for interfaces tag-bone/air and certain mask for reduced colon datasets obtained using anatomical topology amongst the graph of the masks, as detailed in the previously cited co-pending applications. In still a further embodiment, improved computational efficiency may be provided by scanning the elements of the certain soft-tissue mask belonging to the final colon identification mask subsequent to anatomical topology processing of the mask connectivity graph. The main reason for scanning this "layer" is the fact that any lesion will have a dense "inside" depicting characteristics similar to soft tissue, muscle, fat and so on.

In one embodiment detailed thereinafter, at each border element of the object of interest, i.e. the elements inward to the colon in the described case, some resliced planes may be provided in order to investigate a potential trace of a lesion proximate the mucosa of the colon. A trace of a lesion is defined as a connected-labeled component surface not connected to other element belonging to the certain colonic mucosa (U.S. Pat. No. 7,447,342).

In a further embodiment detailed thereinafter, a refined output may be obtained by detecting non-air surfaces depicting a topological hole due to the presence of air inside (typically air bubble inside a false-positive residual untagged stool), or the presence of tagged density within the surface. The skilled addressee will appreciate that this will help refining the initial potential anomaly candidates.

Additionally, in yet another embodiment, the initial potential anomaly candidates may be input on top of any other current methods and systems in order to improve their sensitivity, specifically for the case of small lesions or obstructive lesions that are typically very difficult to identify from typical 3D schemes.

In still a further embodiment, the potential anomaly candidates may be further classified based on a set of features computed for each element of the non-air region. An example of such feature is the density distribution of each element of the non-air region as well as the non-air surface. In fact, using the appropriate masks for starting the analysis and providing the corresponding zones on which the method for isolating is applied eliminates intrinsically any false-positive potentially arising from tagged residuals. This is a great improvement compared to current state-of-the-art methods and systems that require false-positive reduction steps during or after candidate classification. Additionally, potential anomaly candidates may be detected within tagged regions without the necessity to have a proper electronic cleansing method. The method for isolating a potential anomaly is, as a matter of fact, not dependent on the electronic cleansing performance in terms of preserving the colonic mucosa considering it handled the problem in a different way, as it should become apparent to the skilled addressee upon reading of the present description.

In a further embodiment, the skilled addressee will appreciate that each trace of a potential lesion may be analyzed at different window/level in order to increase the certainty of a potential candidate by observing its presence at different "tissue characteristic thresholds".

In still a further embodiment, the detected trace may be further analyzed. In one embodiment, the analysis refers to looking for a topologically closed surface, with no hole. This may ensure no air-bubble is present inside the trace (false-positive), thereby reducing the occurrence of false-positives.

Again, in another embodiment, the step of analyzing the trace comprises the use of a gradient field in order to detect closed surfaces.

Yet in a further embodiment, the analysis of traces may comprise the analysis of the neighboring masks. Neighboring masks, determined from the connectivity graph tree as mentioned above, may be one of Tag/soft tissue or Air/soft tissue masks. On these masks, derivative features depicting the noise/environment behavior may be determined.

In a further embodiment, the layer masks analysis may be used to detect an encircling layer around the initially detected surface. Using such mechanism, the certainty that the candidate is a relevant clinical finding is increased, despite the fact that the neighboring layer can be viewed as "blurry", in depicting an overall behavior encircling soft-tissue. Such behavior is defined as partial volume artifact around a lesion and reinforces the relevance of the trace, as it will be further detailed below.

Based on the two co-pending applications previously cited on the identification of hollow organs wherein no segmentation is used, the present method may be used to only investigate the "thick regions" provided by the non-segmentation process. Notwithstanding that only the present method may be implemented with non-segmented organ, such combination would dramatically decrease the required processing time.

Applications of the method for colorectal lesions detection will now be described with reference to FIGS. 3 to 9B which show potential anomalies. The illustrated anomalies have either been optically confirmed polyps, cancers and obstructive cancers, of sizes of 4.5 mm to 40 mm or are false-positives.

In FIG. 3 previously described, a first contouring 310 contouring a certain soft tissue region 306 and a second contouring 312 contouring a certain air tissue region 304 are shown. The region in between is a transition zone 308 which is a highly uncertain region.

It is worth mentioning that, as illustrated in FIG. 3 and as previously described, a property of a given suspicious region is to depict a concentric certain tissue type region surrounded by a certain air type region. Indeed, a topological property expected for hollow organ is that there is no flying element inside the hollow tube, specifically during a 2D analysis. It may however be anticipated that the ileocaecal valve may most probably appear as such "flying object" as it is the only irregular colonic mucosa region of the colon, as it should be apparent to the skilled addressee. As such, it can be processed accordingly, as explained in U.S. Pat. No. 7,440,601.

Figure 4:
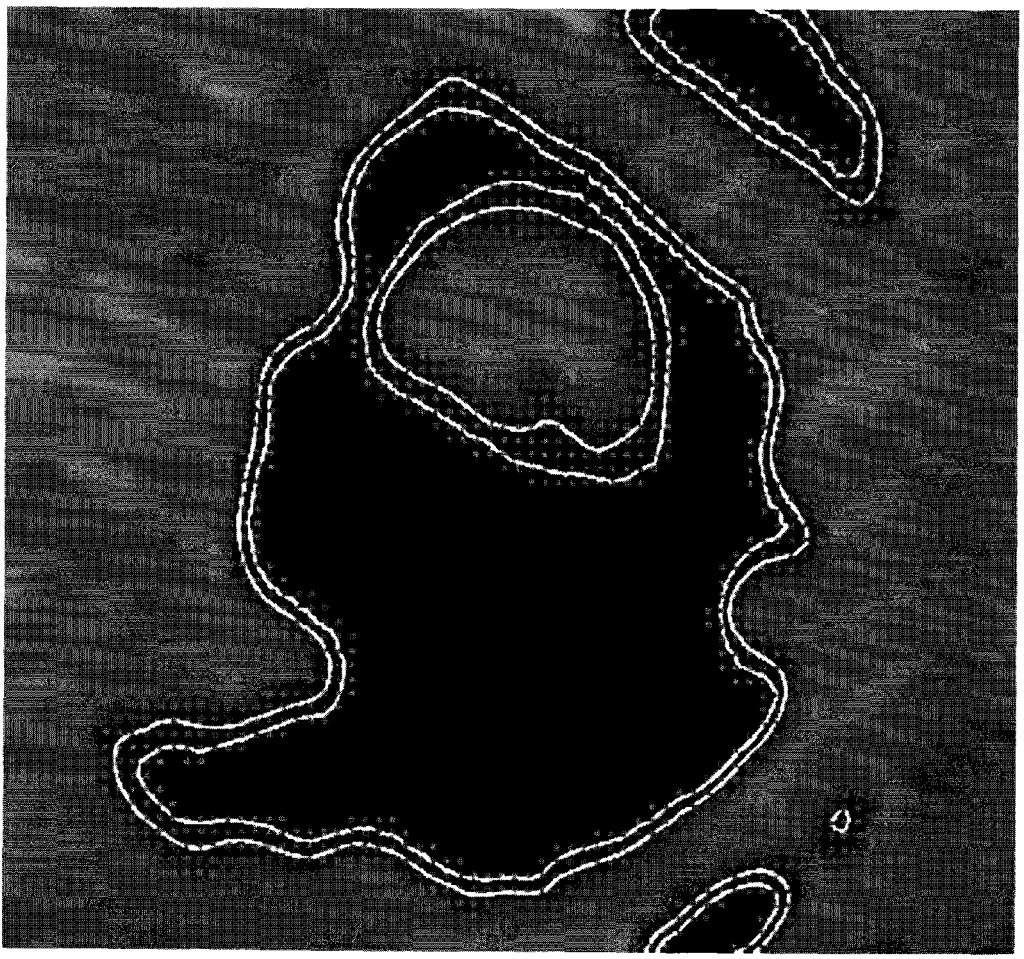
FIG. 4 is an enlarged view of FIG. 3.

Now referring to FIG. 4, sample elements in and around the uncertain region, i.e. the transition zone, have been illustrated. These sample points may be used for isolating the potential anomaly, as described below.

Figure 5:
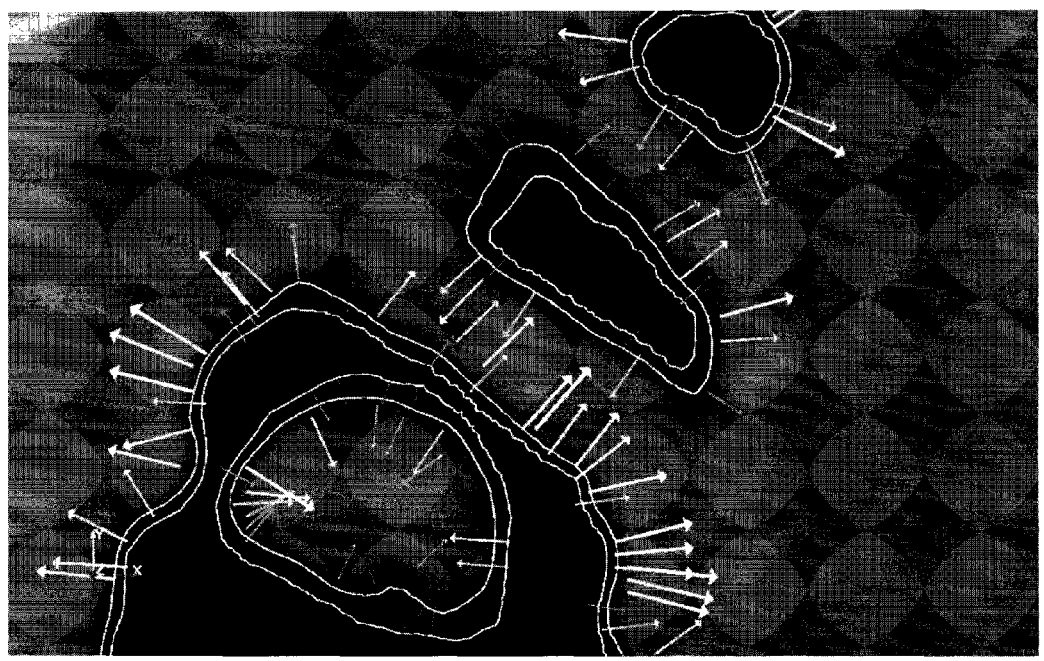
FIG. 5 is another CT scanned image showing a portion of a colon, according to another embodiment.

Now referring to FIG. 5, there is shown computed sampled gradient vectors originating from the sampled points presented in FIG. 4 proximate the uncertain region. This computing enables to determine whether or not the property in the transition zone is concording in order to detect and isolate a potential anomaly. In fact, the skilled addressee will appreciate that the objective of this processing step is to make the most out of the coherent information of the uncertain region.

In this example, it will be appreciated that the uncertain region surrounding the colonic mucosa (the transition zone) depicts a gradient going inward, i.e. penetrating inside the soft tissue and surrounding organs. As well, it can be seen that the uncertain region 308 surrounding the lesion 306 indicates a coherent concentration of denser tissues inside the potential findings. Using the coherent information of the uncertain region, it is possible to highlight physiological properties of lesions, e.g. homogeneous and coherent gradient property of concentric denser tissue originating from the uncertain region. The skilled addressee will therefore appreciate it may be possible to derive pertinent information using uncertain regions coherent information.

It will be appreciated that, as mentioned above, this method is radically different from prior art methods which try, by every means, to decrease the impact of volume artifacts and develop processes of smoothing and summations to attenuate noise interferences. Indeed, prior art methods try to detect a boundary and use these boundary points and possibly the enclosed points for the processing. These methods do not use the uncertain points. On the contrary, in one embodiment of the present method disclosed, the gradient analysis of uncertain regions is used in order to extract, for example, potential coherent information of concentric denser tissue attenuation at specific locations. Specifically, it will be appreciated by the skilled in the art that, in one embodiment, most of the elements of calculations for the gradient calculation originate from a thick-region of uncertain elements as opposed to the use of enclosed elements of segmented region (certain elements) for current state-of-the-art inventions.

The skilled addressee will appreciate that, in a further embodiment, a property of a suspicious region may be to depict a concentric certain tissue type region surrounded by a certain tag type region, for which the property identifier could be an increasing concentric gradient on the region's voxels' density. This later embodiment is the earlier embodiment reciprocal for tagged-patient detection analysis that does not require electronic cleansing.

Figure 6:
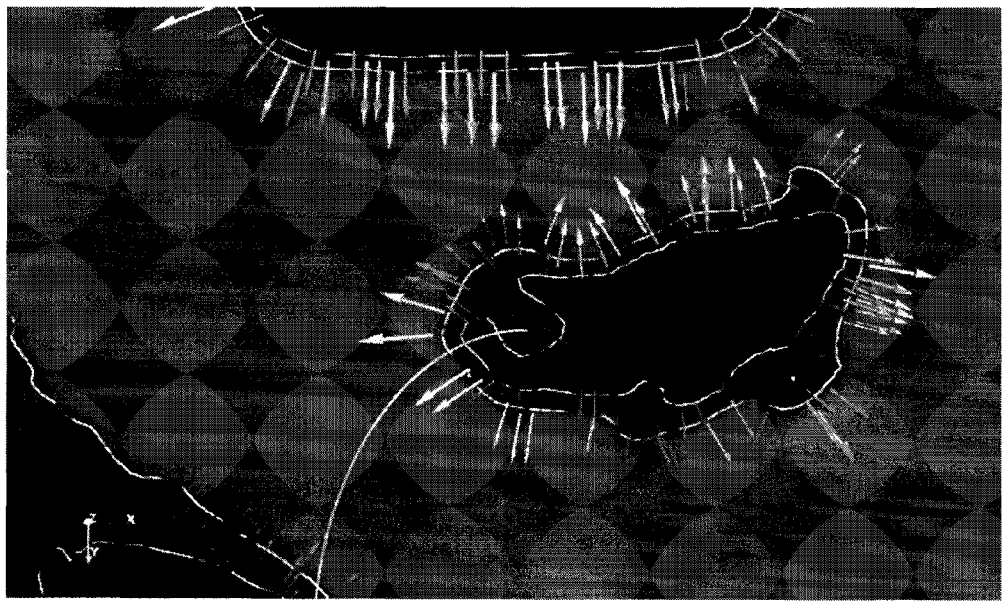
FIG. 6 is another CT scanned image showing a portion of a colon, according to another embodiment.

Now referring to FIG. 6, another exemplary embodiment of the method for isolating a potential anomaly will be described. This Figure illustrates the application of the gradient analysis approach involved in FIG. 5 that may prevent the accrual of false-positives requiring further false-positive-reduction processing steps. A "false-positive" element 600 mimicking a potential protuberance of the colonic mucosa in the colon lumen is shown. Such protuberance would be defined as a positive CAD finding by current methods based on shape analysis (curvature-based or gradient-shock-based). On the contrary, using the principle of the present method for isolating a potential anomaly, it may be seen that a gradient analysis of the surrounding uncertain region does not suggest a coherent soft tissue concentration. In addition, the two certain layers (air and soft tissue) do not end up to create a certain tissue region surrounded by a certain air region as it was presented in FIG. 5 for example. This illustrates that the present method may enable combining detection and false-positive reduction processing steps during a single analysis, which is of great advantage. The skilled addressee will also appreciate that the method may reduce processing time, which is also of great advantage.

Figure 7A:
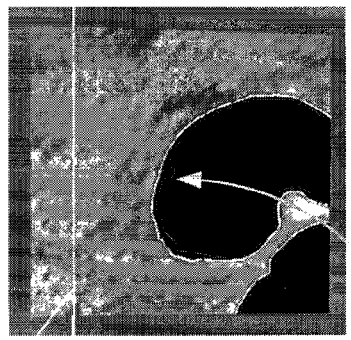
Figure 7A:
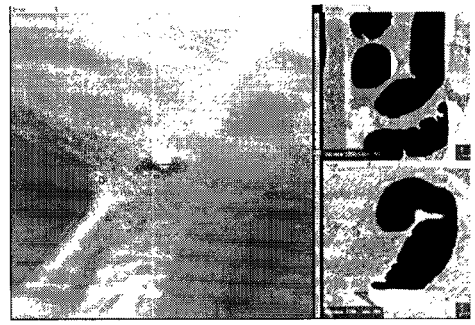
Figure 7C:
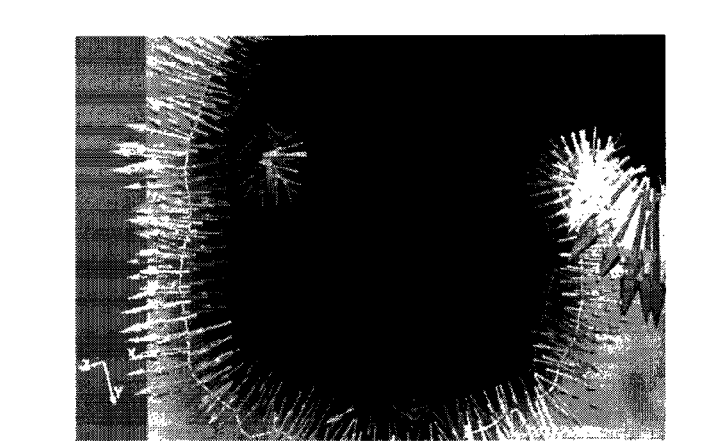
Figure 7D:
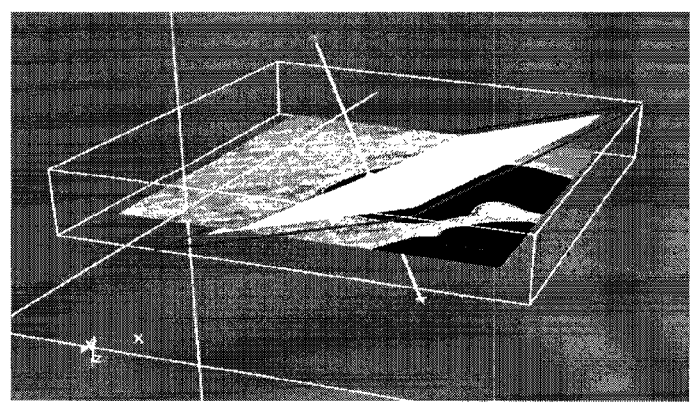

Now referring to FIG. 7A to 7D, a small 4.5 mm polyp 700 is illustrated. FIG. 7B shows that the raw axial image does not provide sufficient information to further identify this small polyp as the certain air layer does not encircle a certain tissue region, as it was illustrated in FIG. 5. In this case, a reslicing processing step that resliced planes at different angles at the certain air border may be implemented. One such resliced image is shown in FIG. 7C and in FIG. 7D as a white plane. On this resliced image shown in FIG. 7C, it is now possible to identify an air region encircling, not a tissue region but an uncertain region.

As shown in FIG. 7C, gradient properties determined from this encompassed region shows a tendency of soft tissue, that was further validated by the Gradient certain threshold property. Once again, the information of the uncertain region provides enough properties to determine a true CAD positive finding revealing a true 4.5 mm polyp. Again, this is derived from the nature of one type of lesions and polyps that have soft tissue or denser tissue at their center, in a uniform distribution.

Figure 8:
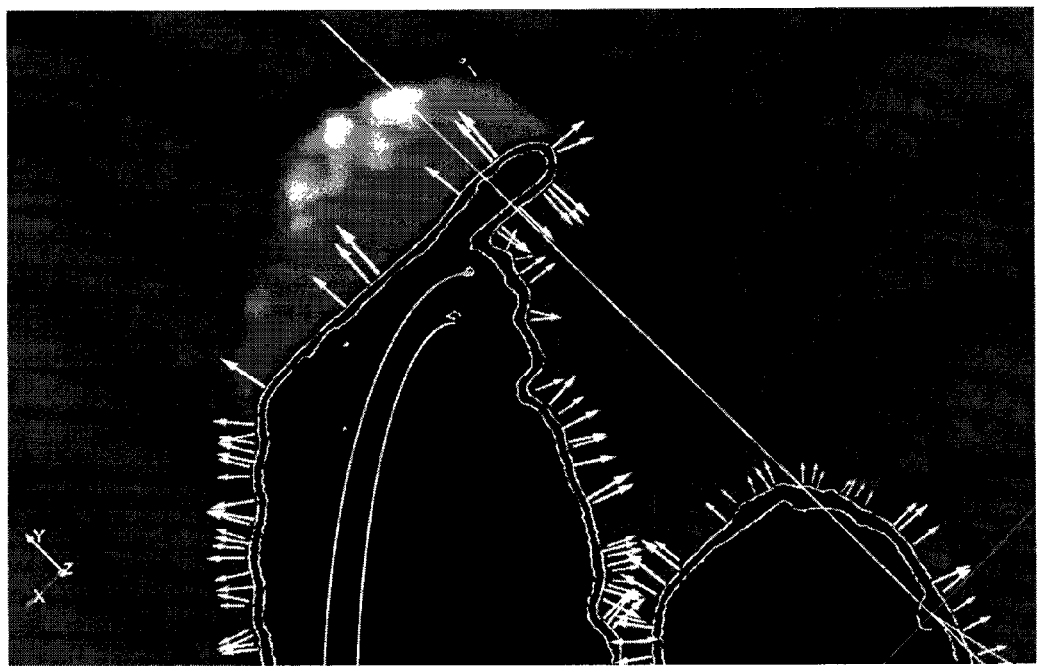
FIG. 8 is another CT scanned image showing a portion of a colon, according to another embodiment.

Now referring to FIG. 8, there is better illustrated the behavior of one embodiment of the present method involving the gradient property analysis. In a manner similar to FIG. 3, some small uncertain regions 800 are encircled by a certain air region. The analysis of the gradient of such regions revealed false positive findings. This shows the robustness of the present method that leverages uncertain regions information to discard false positive candidates in a processing step equivalent to that of identifying positive CAD findings. Such combination of two steps in one allows improving processing speed, which is of great advantage.

Figure 9A:
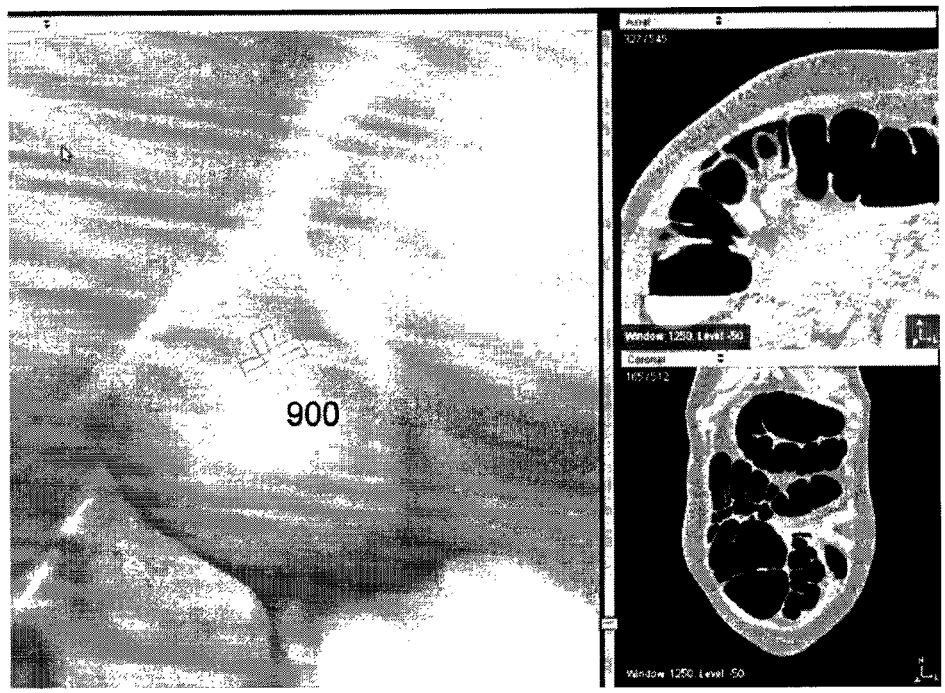
FIGS. 9A and 9B show images representative of another portion of a colon, according to another embodiment.
Figure 9B:
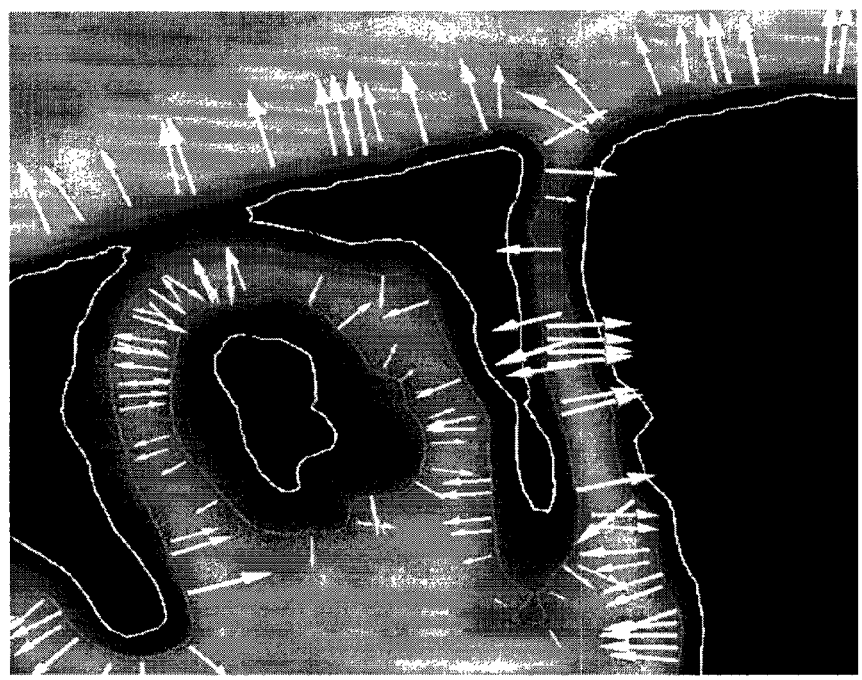

Now referring to FIGS. 9A and 9B, another embodiment of the method which helps avoiding pitfalls and false positives depicted by current state-of-the-art morphological CAD processes will be described. As depicted on the left of FIG. 9A, a spherical-like shape 900 in the colon lumen can be seen, and would further be reported as a CAD finding for current state-of-the-art strategies. On the contrary, the present method would inherently classify such region as being a false-positive considering the candidate region is filled with air, as illustrated in FIG. 9B. Indeed, analyzing the gradient of the uncertain region in between air/tissue, it may be seen that the gradient indicate folds and colonic mucosa, but no concentration of certain tissue gradient at the center of the "spherical candidate region" considering it is filled with air. This discards such region as being a reported potential CAD finding.

Figure 10:
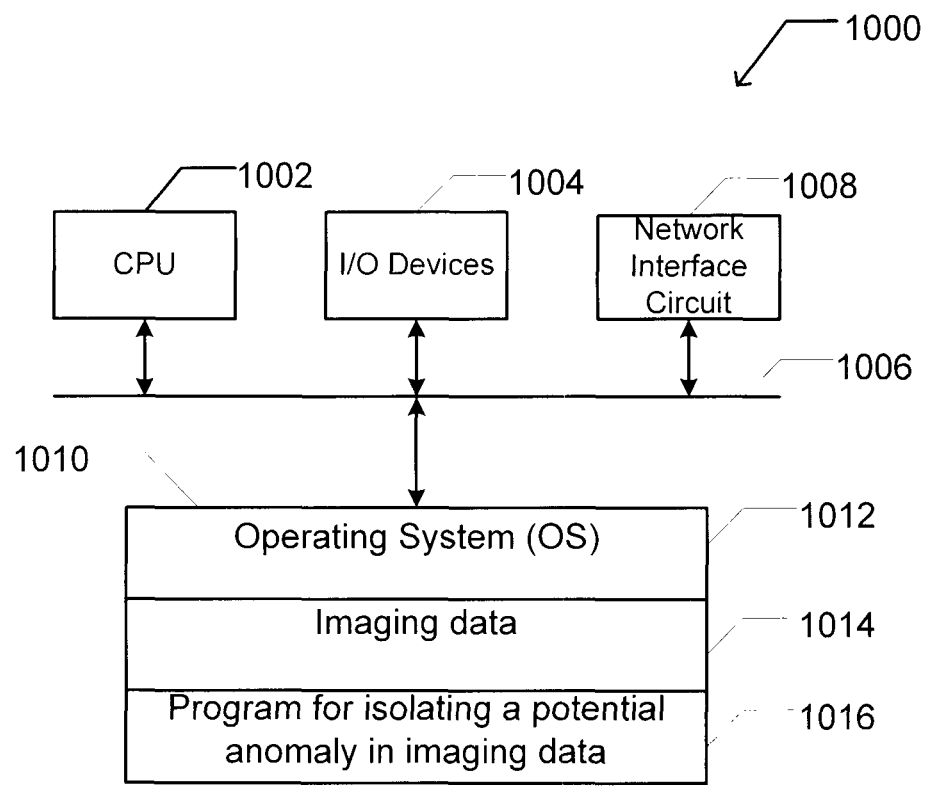
FIG. 10 is a block diagram showing an embodiment of a processing device in which the method for isolating a potential anomaly in imaging data may be implemented.

Now referring to FIG. 10, there is shown an embodiment of a processing device 1000 in which the method for isolating a potential anomaly in imaging data may be advantageously used.

The processing device 1000 comprises a central processing unit 1002, I/O devices 1004, a network interface circuit 1008, a data bus 1006 and a memory 1010. The central processing unit 1002, the I/O devices 1004, the network interface circuit 1008 and the memory 1010 are operatively coupled using the data bus 1006.

More precisely, the central processing unit 1002 is adapted for processing data instructions. The network interface circuit 1008 is adapted for operatively connecting the processing device 1000 to another processing device (not shown) via a data network (not shown). The skilled addressee will appreciate that various embodiments of the network interface circuit 1008 may be provided. Moreover, the skilled addressee will also appreciate that the network interface circuit 1008 may operate according to various communication protocols such as TCP/IP for instance.

The I/O devices 1004 are used for enabling a user to interact with the processing device 1000. The skilled addressee will appreciate that various embodiments of the I/O devices 1004 may be used. For example, the I/O devices 1004 may comprise at least one of a keyboard, a screen and a mouse.

The skilled addressee will also appreciate that various embodiments of the data bus 1006 may be provided.

It will also be appreciated that various embodiments of the memory 1010 may be provided. Moreover, it will be appreciated that the memory 1010 may be used to store, in one embodiment, an operating system 1012, at least one program for isolating a potential anomaly in imaging data 1016, wherein the at least one program is configured to be executed by the central processing unit 1002, and databases 1014 used for operating the at least one program for isolating a potential anomaly in imaging data 1016.

In one embodiment, the at least one program for isolating a potential anomaly in imaging data 1016 comprises instructions for providing a set of at least one given anomaly property representative of a given anomaly.

The at least one program for isolating a potential anomaly in imaging data 1016 further comprises instructions for providing an anomaly property identifier for identifying each of the at least one given anomaly property.

The at least one program for isolating a potential anomaly in imaging data 1016 further comprises instructions for isolating, in the imaging data, a first zone having a first property and a group of at least one other zone, each of the at least one other zone having a corresponding property different than the first property.

It will be appreciated that the imaging data may be stored in the databases 1014. The imaging data may be obtained from at least one of the I/O devices 1004 and the network interface circuit 1008.

The at least one program for isolating a potential anomaly in imaging data 1016 further comprises instructions for providing a transition zone resulting from the isolation of a first zone and a group of at least one other zone, the transition zone being selected from a group consisting of a closed zone separating the first zone and the group of at least one other zone and a closed zone extending in one of the first zone and the group of at least one other zone.

The at least one program for isolating a potential anomaly in imaging data 1016 further comprises instructions for applying the anomaly property identifier for identifying each of the at least one given anomaly property on at least the transition zone for providing a computed indication for a selected zone, the selected zone being at least the transition zone.

The at least one program for isolating a potential anomaly in imaging data 1016 further comprises instructions for determining if the computed indication for the selected zone is concording with each of the at least one given anomaly property and if the computed indication for the selected zone is concording, for assigning an indication of potential anomaly candidate zone to the selected zone to thereby isolate the potential anomaly.

The skilled addressee will appreciate that the operating system 1012 is used for managing the interactions between the central processing unit 1002, the I/O devices 1004, the network interface circuit 1008, the data bus 1006 and the memory 1010.

Figure 11:
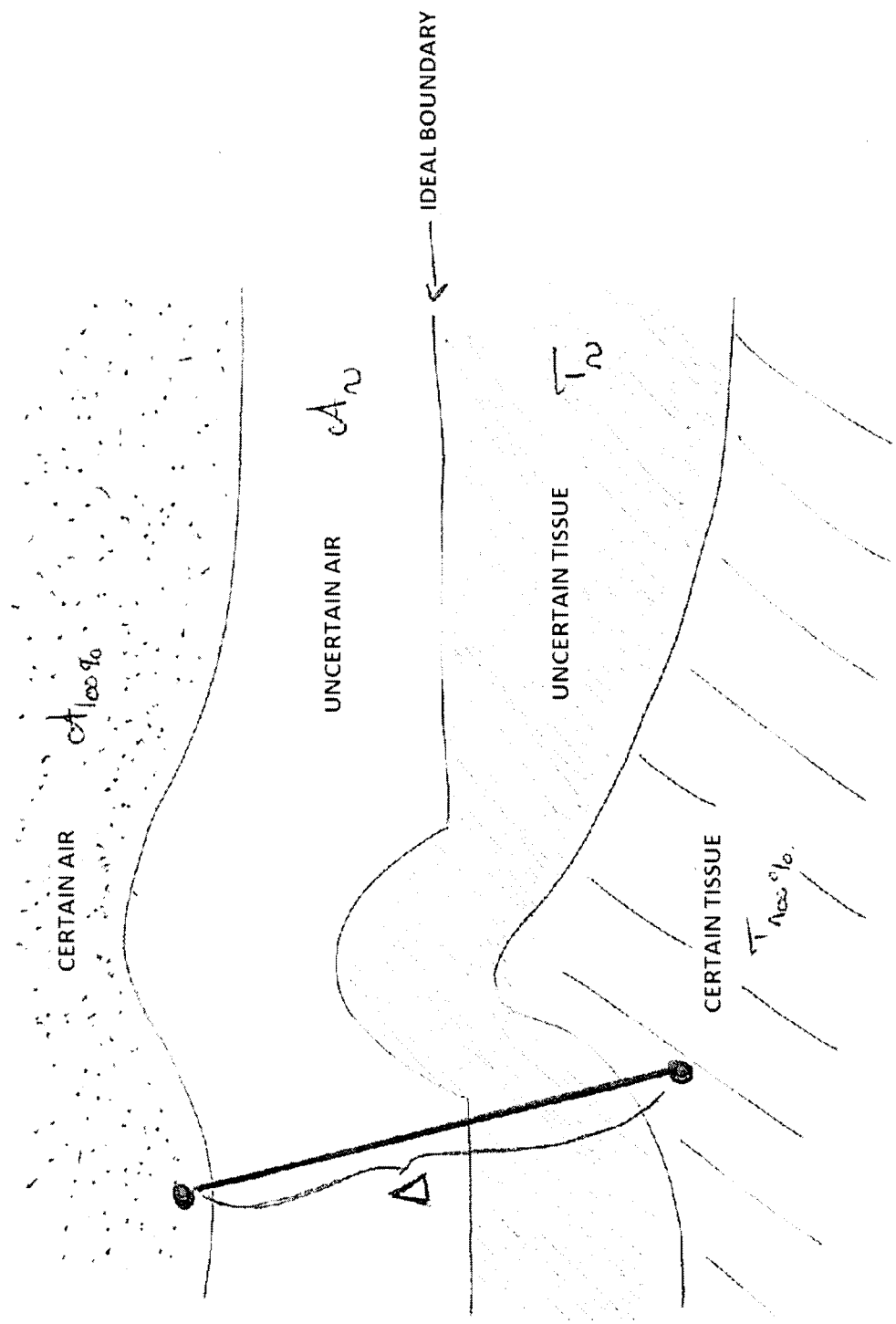
FIG. 11 is a schematic showing an embodiment in which a thick region of investigation is determined, for example extending from the certain air region toward the certain tissue region, for a distance Δ.

In a preferred embodiment, a singularity analysis is performed to decrease the number of elements where cutting-planes analysis is performed as expressed above. As illustrated in FIG. 11, a thick region of investigation is determined, for example extending from the certain air region toward the certain tissue region, for a distance $\Delta$. In one embodiment, $\Delta$ relates to the characteristic of the singularities to be identified. For the specific case of colorectal lesions, $\Delta$ is determined so that singularities would exist for both the smallest and the largest anomalies to be reported.

In one embodiment, the singularity analysis is a process optimizing the detection of potential anomalies while making sure that all of the potential anomalies to be reported are encompassed by the thick region under examination.

Figure 12:
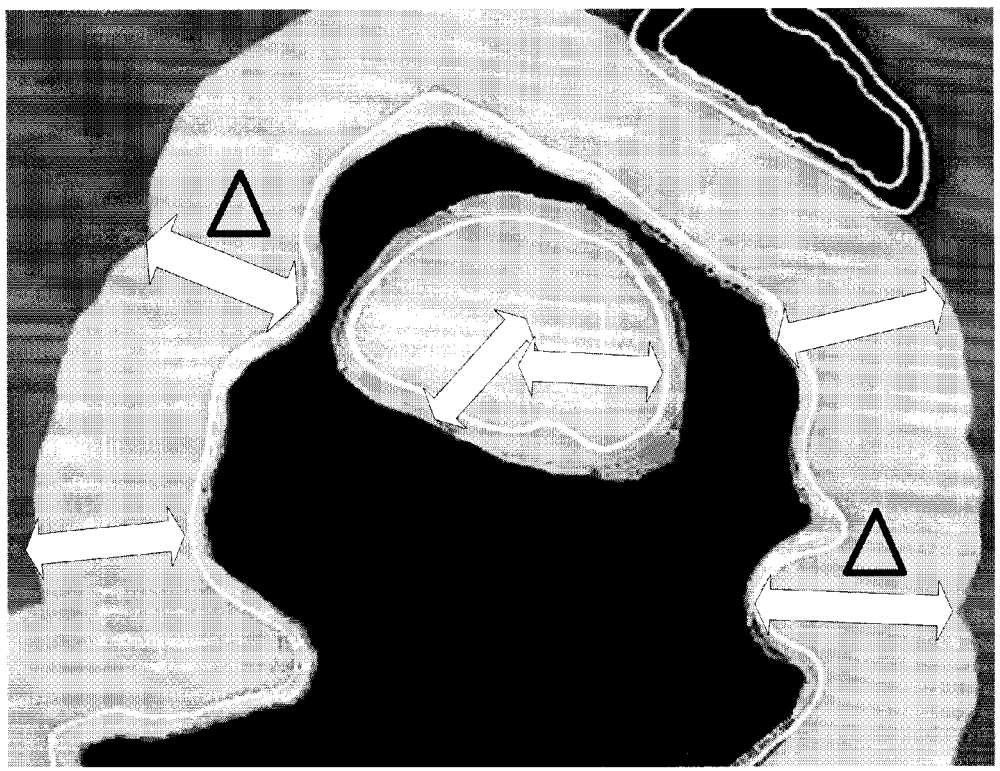
FIG. 12 is an enlarged view of a part of a CT scanned image showing a portion of a colon shown in FIG. 3.

Now referring to FIG. 12, there is shown a 2D image of the colon, where the red border determines the certain air region, and the yellow border represents the $\Delta$ Thick region extending from the certain air region.

It will be appreciated that in a further embodiment, the singularity analysis is performed through a distance transform process applied on the extended thick region. Such distance transform could be a Euclidean Distance Transform or a Weighted Transform as detailed in "R. Kimmel and al., Sub-pixel Distance Maps and Weighted Distance Transforms, Journal of Mathematical Imaging and Vision, 1994". In this process, the determination of singularities will comprise two processing steps. A first processing step is the identification of local maxima on the distance map while a second processing step is the discarding of local maxima with low potential of belonging to an anomaly.

Figure 13:
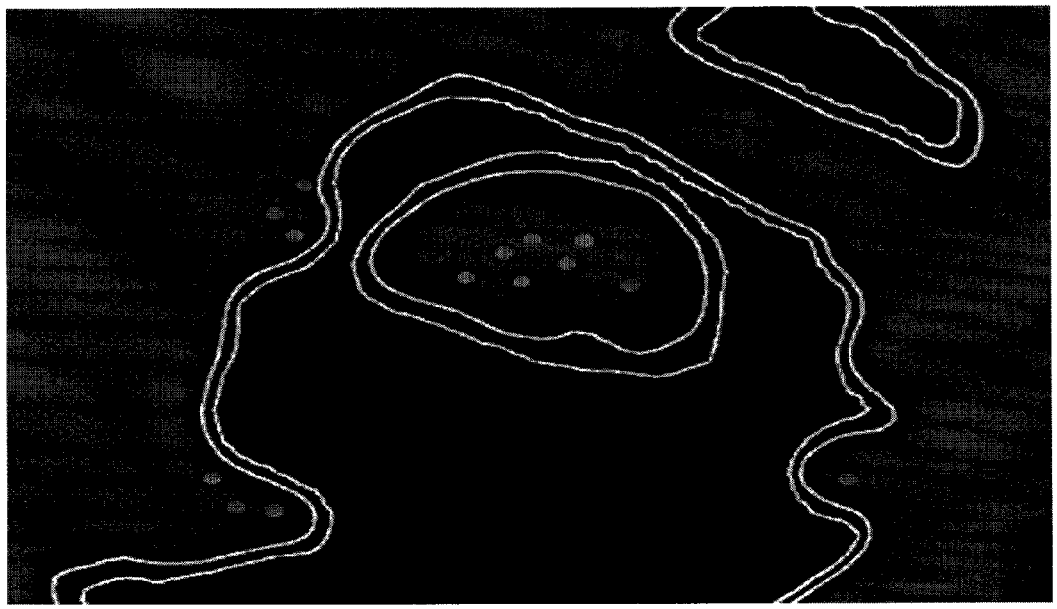
FIG. 13 is an enlarged view of a part of a CT scanned image showing a portion of a colon shown in FIG. 3 wherein local maxima present in the extended thick region at a constant distance Δ from the certain air region are shown.

Now referring to FIG. 13, there are illustrated local maxima present in the extended thick region at a constant distance $\Delta$ from the certain air region. It can be observed that such embodiment decreases dramatically the number of elements to be further analyzed through a cutting-planes methodology which is of great advantage.

In an alternative embodiment, the number of local maxima may be further reduced using rays extending from the certain air region toward the certain tissue region. These rays carry intensity strength that decreases the further they extend from the certain air region. In a further embodiment, these rays may have strength profile accounting for the elements intensities along the rays. Each of these rays is normal to the certain air border.

Figure 14:
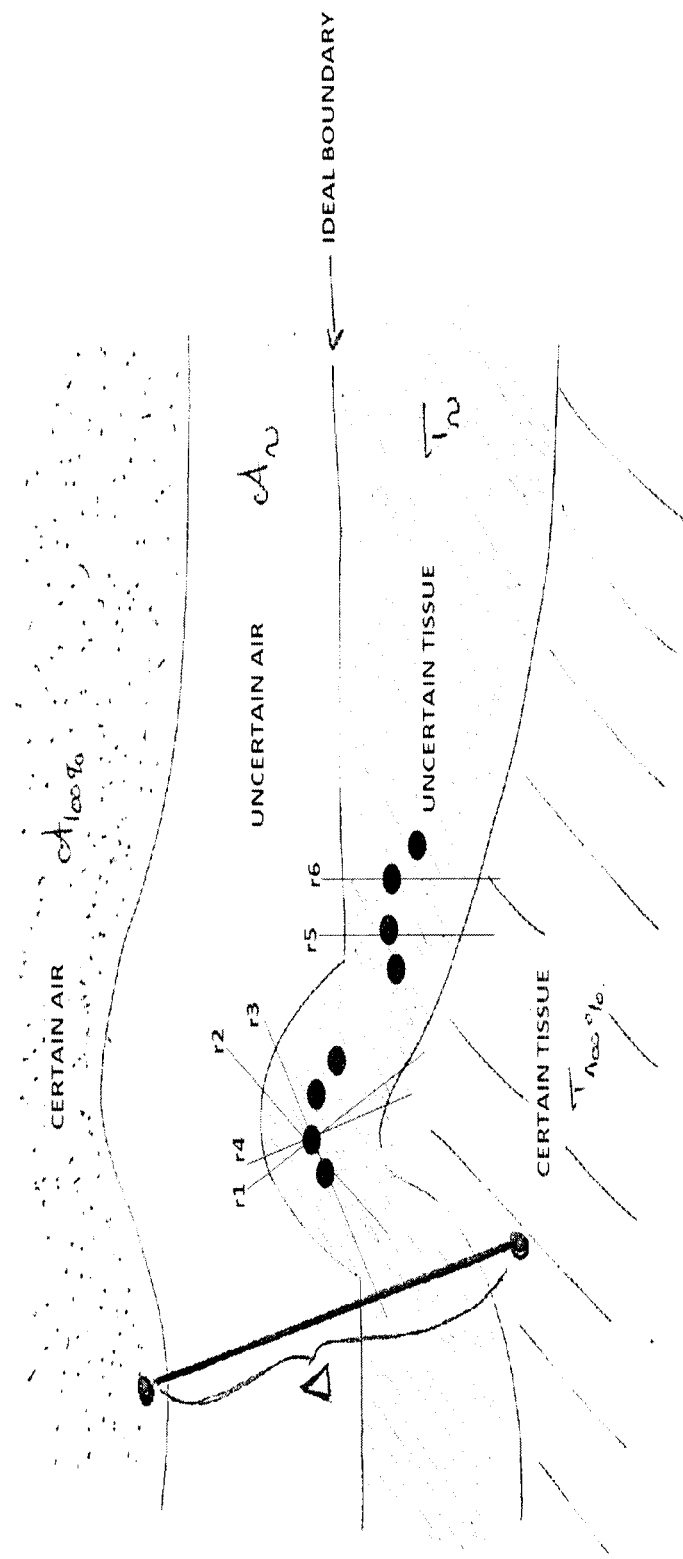
FIG. 14 shows the schematic of FIG. 11 with final singular points obtained by casting rays and performing a reduction process on local maxima by thresholding the accumulation of Ray-strength at a given magnitude.
Figure 15:
FIG. 15 is an enlarged view of a part of a CT scanned image showing a portion of a colon shown in FIG. 3 wherein exemplary rays orthogonal to the certain air region and passing through singular points have been casted. It can be seen that these rays intersect at singular points most probably belonging to potential anomalies.
Figure 16:
FIG. 16 is an enlarged view of a part of a CT scanned image showing a portion of a colon shown in FIG. 3 wherein singular points have been further discriminated by applying a "strength" threshold at each rays intersections; the more rays culminating at a singular point, the more strength, and the more probability of that singular points belonging to a potential anomaly
Figure 17:
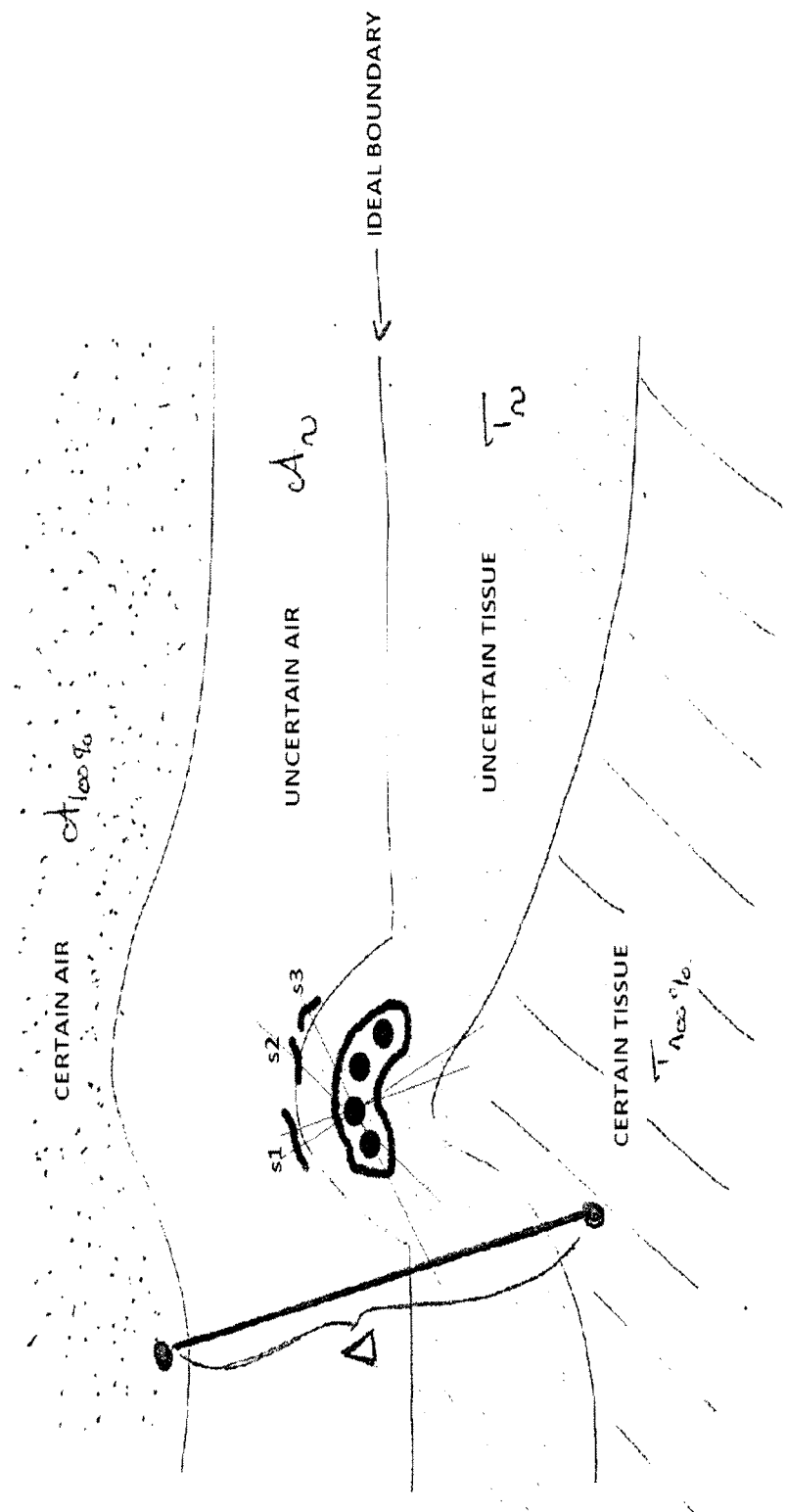
FIG. 17 is the schematic of FIG. 11 wherein singular points can be clustered so as to reconstruct portions of an approximate colonic mucosa at the potential anomaly location, casting outward rays from the clusters of at least one singular point, and involving the previously determined distance transform map. Such portions of approximate colonic mucosa at potential anomaly locations can be further used to determined an approximate center of gravity (for 3D evaluation using a center of rotation for example) and approximate measurement of potential lesions.

It is therefore possible to obtain final singular points, as shown in FIG. 14, by casting rays and performing a reduction process on the local maxima by thresholding the accumulation of Ray-strength at a given magnitude.

These final singular points are further used for centering the cutting-planes described above. The skilled addressee will appreciate that these embodiments significantly reduce the cutting-planes process, since they are performed only on localized elements, and are not relying on the accurate segmentation of the colonic mucosa, which is of great advantage.

Figure 18A:
FIG. 18A is an enlarged view of a part of a CT scanned image showing a distance field extending from certain air regions toward certain tissue regions. Unlike traditional distance transform approaches that converge toward the center of an object, the extending distance objective is to provide information on how far certain tissue regions are from certain air regions. Such extension is constrained by a maximum penetration thickness depending on the "anomaly property size".
Figure 18B:
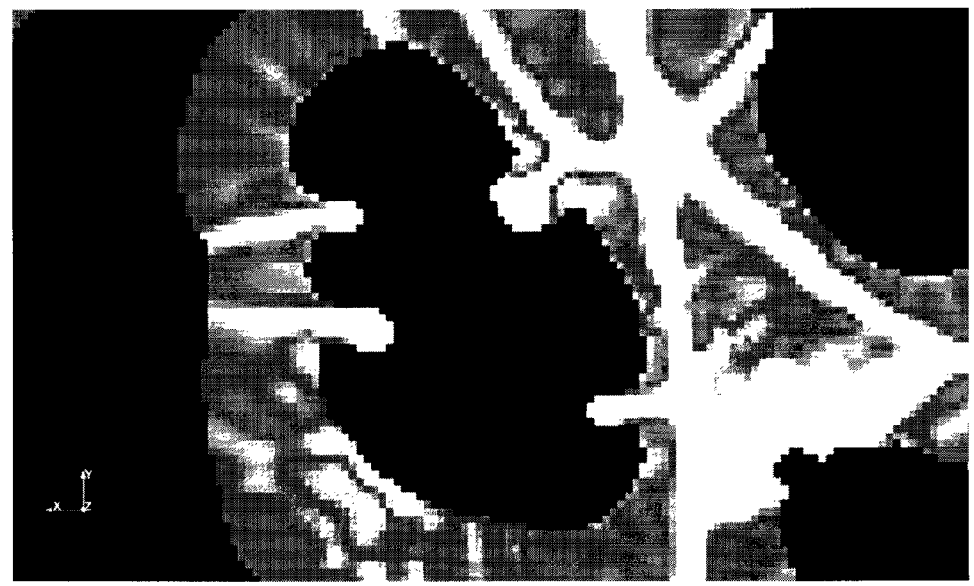
FIG. 18B is an enlarged view of a part of a CT scanned image showing a surface flux determined from, and extending within, a distance field extension such as presented in FIG. 18A. Such surface flux will provide information on the localization of local maxima. The person skilled in the art will appreciate that the combination of both information maps (i.e.

In a further embodiment, and as illustrated in FIGS. 18A and 18B, the singularity analysis involves the processing step of extending a distance field from a first certain air region into a certain tissue region, constrained within a given thickness that is determined based on the anomaly property size. The resulting thick region carrying the distance field information would represent the transition zone in which potential anomalies could be identified. In a further embodiment, the singularity analysis would involve the determination of a surface flux extending within the thick distance field extending from certain air regions into certain tissue regions. In yet a further embodiment, the combination of both the distance field extension and the surface flux would allow the determination of local maxima at locations where the surface flux is singular and at a given distance representing the potential anomaly property size.

The one skilled in the art will recognize that such method would inherently discard regions with air bubbles and does not require an accurate segmentation of the colonic mucosa. In addition, the one skilled in the art will recognize that the support involved to determine the distance field extension and surface flux determination could be filtered by a bilateral filter, eventually making the most of strong a priori from the certain-air and certain-tag and certain tissue regions affecting the weights of such bilateral filters, providing that shapes are maintained within the thick transition region, and disregarding potential artifacts away from the thick region.

FIG. 18A presents a distance field extending from certain air regions toward certain tissue regions. Unlike traditional distance transform approaches, the extending distance objective is to provide information on how far certain tissue regions are from certain air regions, and are extends constrained by a maximum penetration thickness depending on the "anomaly property size".

FIG. 18B presents a surface flux determined from, and extending within, the distance field extension. Such surface flux will provide information on the localization of local maxima. The skilled in the art will understand that the combination of both information maps would discard false-positives due to air bubbles closed to the surface, potentially resulting from air in remnant stools for example.

It will be appreciated that in a further embodiment, these local maxima may be used in order to address the issue of 3D camera positioning. In fact, positioning automatically a camera in 3D, so as to support the reader's examination, is not possible since the colonic mucosa is not accurately determined and since the embodiments disclosed do not rely on, nor output, the accurate segmentation of the colonic mucosa, and thus that of potential anomalies. However, it is possible to support the review of radiologists by defining these final local maxima as center of rotations for 3D camera by leveraging on the fact that these final local maxima are within potential anomalies, specifically centered at their denser regions.

Figure 19:
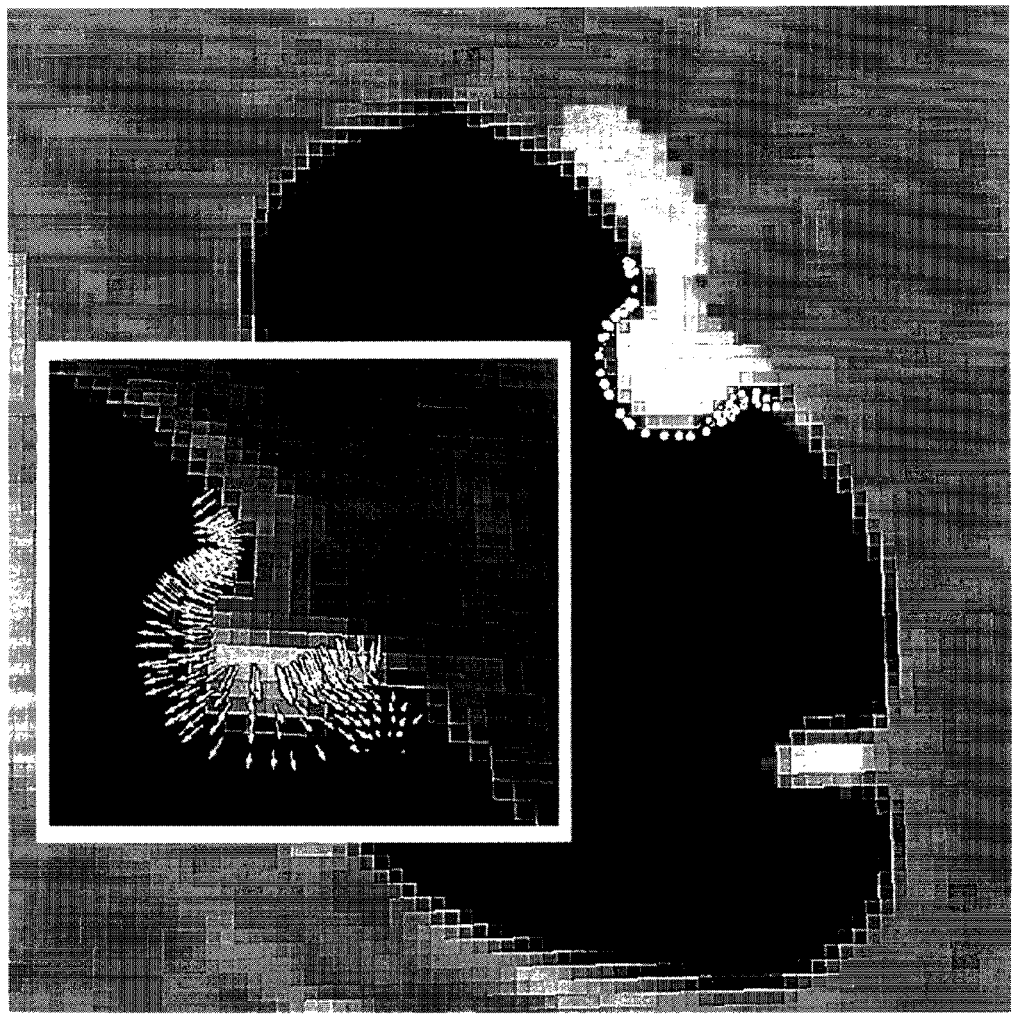
FIG. 19 illustrates a 2-dimensional image originating from a CT Colonography exam.

In yet a further embodiment, and referring to FIG. 19, an inverse problem is carried on the rays passing through each of the final local maxima or their clustering, if closed enough. This inverse problem is aimed at the reconstruction of at least one part of the colonic mucosa. The skilled addressee will appreciate that multiple inverse approaches may be used such as an implicit surface problem based on the distance information of singular points that are defined as "most probably accurate". In a further embodiment, these patches of surfaces are used to visually support the analysis of the potential anomaly by depicting specific colors on either 2D or 3D to mark such regions. These embodiments allow to bypass the issue that it was not possible to mark the potential anomaly during image rendering because no accurate segmentation of the colon is performed.

FIG. 19 illustrates a 2-dimensional image originating from a CT Colonography exam. The main image presents two regions under investigations (the two protuberant ones), wherein one depicts a local maxima. From that local maximum, an inverse problem is carried on in order to determine an implicit surface best representing a reconstructed colonic mucosa at that specific region. Such implicit surface is presented in the left enlarged image in which one can see the coarse pixels of the original image, and the refined reconstructed colonic mucosa implicit surface that may be used to determine the regions's of interests thickness and volume.

In one embodiment, the reconstructed patches of anomalies are used for determining an approximate measurement of the anomaly.

Finally, although the skilled addressee will appreciate that the previous embodiments allows to overcome the limitations of a scheme that does not involve any accurate and traditional segmentation process, specifically in supporting the visual examination of potential anomalies, the skilled addressee will also appreciate that these embodiments can be used without the cutting-plane embodiments.

Although the above description relates to specific preferred embodiments as presently contemplated by the inventor, it will be understood that the invention in its broad aspect includes mechanical and functional equivalents of the elements described herein.

The invention claimed is:

1. A computer-implemented method for isolating a potential anomaly in imaging data, the computer-implemented method comprising:

providing a set of at least one given anomaly property representative of a given anomaly;

providing an anomaly property identifier for identifying each of the at least one given anomaly property;

in the imaging data, isolating a first zone characterized by a first certain property and a group of at least one other zone, each of the at least one other zone characterized by a corresponding certain property different than the first certain property, wherein the first certain property of the first zone and the corresponding certain property of the at least one other zone characterize with unambiguity the first zone and the at least one other zone, respectively;

indicating a transition zone located in the imaging data and resulting from the isolation of a first zone located in the imaging data and a group of at least one other zone located in the imaging data, wherein the at least one given anomaly property can be described as a function of the transition zone, wherein the transition zone is characterized by an uncertain property, the transition zone being selected from a group consisting of:

a closed zone separating the first zone and the group of at least one other zone; and a closed zone extending in one of the first zone and the group of at least one other zone;

applying the anomaly property identifier for identifying each of the at least one given anomaly property on at least the transition zone for providing a computed indication for a selected zone, the selected zone being at least the transition zone;

determining if the computed indication for the selected zone is concording with each of the at least one given anomaly property; and if the computed indication for the selected zone is concording, assigning an indication of potential anomaly candidate zone to the selected zone to thereby isolate said potential anomaly.

2. The computer-implemented method as claimed in claim 1, wherein the imaging data comprise a n-dimensional dataset originating from an imaging system, wherein n is greater or equal than two.

3. The computer-implemented method as claimed in claim 2, wherein the n-dimensional dataset is one of a 2-dimensional volumetric array of elements and a 3-dimensional volumetric array of elements.

4. The computer-implemented method as claimed in claim 2, wherein the n-dimensional dataset originates from a device selected from a group consisting of a magnetic resonance imaging (MRI) device, a positron emission tomography (PET) device, an X-Rays device, an ultrasound device and any combination thereof.

5. The computer-implemented method as claimed in claim 1, wherein the set of at least one given anomaly property comprises at least one of composition related information, shape related information, spatial localization in the imaging data, and a combination thereof over time.

6. The computer-implemented method as claimed in claim 1, wherein the anomaly property identifier comprises at least one of tissue density determination, homogeneity of tissue gradient determination, determination of absence or presence of tissue properties, determination of water content/distribution, determination of presence and determination of a distribution of contrast agent at a given moment or over time.

7. The computer-implemented method as claimed in claim 1, wherein the first certain property of the first zone comprises certain air region, further wherein the corresponding certain property of each of the at least one other zone comprises certain tissue region.

8. The computer-implemented method as claimed in claim 1, wherein the first certain property of the first zone comprises certain tagged region, further wherein the corresponding certain property of each of the at least one other zone comprises certain tissue region.

9. The computer-implemented method as claimed in claim 1, further comprising applying the anomaly property identifier to the selected zone.

10. The computer-implemented method as claimed in claim 1, further comprising providing an indication of a potential anomaly.

11. The computer-implemented method as claimed in claim 10, wherein the providing of an indication of a potential anomaly comprises at least one of storing the indication of a potential anomaly and displaying the indication of a potential anomaly on a user interface.

12. The computer-implemented method as claimed in claim 10, further comprising transmitting the indication of a potential anomaly to a remote location.

13. The computer-implemented method as claimed in claim 1 wherein said image data comprises a plurality of unitary image elements selected from the group consisting of pixels and voxels.

14. A non-transitory computer readable medium having instructions recorded thereon for performing the method for isolating a potential anomaly in imaging data as claimed in claim 1.

15. A computer-implemented method for isolating a potential anomaly in imaging data, the computer-implemented method comprising:

receiving imaging data;

isolating in the imaging data a first zone characterized by a first certain property and a group of at least one other zone, each of the at least one other zone characterized by a corresponding certain property different than the first certain property, wherein the first certain property of the first zone and the corresponding certain property of the at least one other zone characterize with unambiguity the first zone and the at least one other zone, respectively;

indicating a transition zone located in the imaging data resulting from the isolation of a first zone located in the imaging data and a group of at least one other zone located in the imaging data, wherein the at least one given anomaly property can be described as a function of the transition zone, wherein the transition zone is characterized by an uncertain property, the transition zone being selected from a group consisting of:

a closed zone separating the first zone and the group of at least one other zone; and a closed zone extending in one of the first zone and the group of at least one other zone;

applying an homogeneity of tissue gradient identifier on at least the transition zone for providing a computed indication for a selected zone, the selected zone being at least the transition zone;

determining if the computed indication is concording for the selected zone; and if the computed indication for the selected zone is concording, assigning an indication of potential anomaly candidate zone to the selected zone to thereby isolate said potential anomaly.

16. A system for isolating a potential anomaly in imaging data, the system comprising:

a data bus;

a central processing unit operatively connected to the data bus;

an I/O device operatively connected to the data bus;

a network interface circuit operatively connected to the data bus; and a memory operatively connected to the data bus, the memory comprising at least one program for isolating a potential anomaly in imaging data wherein the at least one program is configured to be executed by the central processing unit, the at least one program for isolating a potential anomaly in imaging data comprising:

instructions for providing an anomaly property identifier for identifying each of the at least one given anomaly property;

instructions for isolating, in the imaging data, a first zone characterized by a first certain property and a group of at least one other zone, each of the at least one other zone characterized by a corresponding certain property different than the first certain property, wherein the first certain property of the first zone and the corresponding certain property of the at least one other zone characterize with unambiguity the first zone and the at least one other zone, respectively;

instructions for indicating a transition zone located in the imaging data resulting from the isolation of a first zone located in the imaging data and a group of at least one other zone located in the imaging data, wherein the at least one given anomaly property can be described as a function of the transition zone, wherein the transition zone is characterized by an uncertain property, the transition zone being selected from (i) a group consisting of a closed zone separating the first zone and the group of at least one other zone, and (ii) a closed zone extending in one of the first zone and the group of at least one other zone;

instructions for applying the anomaly property identifier for identifying each of the at least one given anomaly property on at least the transition zone for providing a computed indication for a selected zone, the selected zone being at least the transition zone;

instructions for determining if the computed indication for the selected zone is concording with each of the at least one given anomaly property and if the computed indication for the selected zone is concording, for assigning an indication of potential anomaly candidate zone to the selected zone to thereby isolate said potential anomaly.

17. The system for isolating a potential anomaly in imaging data as claimed in claim 16, wherein the memory further comprises the imaging data.

18. The system for isolating a potential anomaly as claimed in claim 16, wherein the imaging data is received from the network interface circuit.

* * * * *

UNITED STATES PATENT AND TRADEMARK OFFICE
CERTIFICATE OF CORRECTION

PATENT NO. : 9,717,414 B2
APPLICATION NO. : 14/001628
DATED : August 1, 2017
INVENTOR(S) : Florent Andre Robert Chandelier Page 1 of 1

It is certified that error appears in the above-identified patent and that said Letters Patent is hereby corrected as shown below:

On the Title Page

(73) Assignee reads:
DOG MICROSYSTEMS, INC., Granby, Quebec (CA)
Should read:
CADENS MEDICAL IMAGING INC., Granby, Quebec (CA)

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*